US008858441B2

(12) United States Patent
Konofagou et al.

(10) Patent No.: US 8,858,441 B2
(45) Date of Patent: Oct. 14, 2014

(54) SYSTEM AND METHOD FOR ELECTROMECHANICAL WAVE IMAGING OF BODY STRUCTURES

(75) Inventors: Elisa E. Konofagou, New York, NY (US); Mathieu Pernot, Paris (FR)

(73) Assignee: The Trustees of Columbia University in the City of New York, New York, NY (US)

(*) Notice: Subject to any disclaimer, the term of this patent is extended or adjusted under 35 U.S.C. 154(b) by 970 days.

(21) Appl. No.: 11/433,510

(22) Filed: May 12, 2006

(65) Prior Publication Data

US 2007/0049824 A1    Mar. 1, 2007

Related U.S. Application Data

(60) Provisional application No. 60/680,081, filed on May 12, 2005.

(51) Int. Cl.
*A61B 8/00* (2006.01)

(52) U.S. Cl.
USPC ........................................................ 600/443

(58) Field of Classification Search
USPC ........... 600/437, 442, 444, 450; 382/128, 131
See application file for complete search history.

(56) References Cited

U.S. PATENT DOCUMENTS

| | | |
|---|---|---|
| 3,598,111 A | 8/1971 | Kahn et al. |
| 4,463,608 A | 8/1984 | Takeuchi et al. |
| 4,777,599 A | 10/1988 | Dorogi et al. |
| 4,822,679 A | 4/1989 | Cerdan-Diaz et al. |
| 5,038,787 A | 8/1991 | Antich et al. |
| 5,107,837 A | 4/1992 | Ophir et al. |
| 5,178,147 A | 1/1993 | Ophir et al. |
| 5,309,914 A | 5/1994 | Iinuma |
| 5,433,708 A | 7/1995 | Nichols et al. |
| 5,435,310 A | 7/1995 | Sheehan et al. |
| 5,457,754 A | 10/1995 | Han et al. |
| 5,601,084 A | 2/1997 | Sheehan et al. |

(Continued)

FOREIGN PATENT DOCUMENTS

WO    WO 2011/028690    3/2011

OTHER PUBLICATIONS

Notification of Transmittal of the International Search Report and the Written Opinion of the International Searching Authority, or the Declaration International Application No. PCT/US06/18454 dated Aug. 9, 2007.

(Continued)

*Primary Examiner* — Tse Chen
*Assistant Examiner* — Rochelle Reardon
(74) *Attorney, Agent, or Firm* — Miles & Stockbridge P.C.; Mark A. Catan

(57) ABSTRACT

A system and method for detecting electromechanical wave propagation within a body structure of a patient in a series of image frames representing movement the body structure. Image data is acquired comprising a series of image frames corresponding to the movement of a body structure. A correlation calculation is performed on the image frames to generate a displacement map representing the relative displacement between the first and second image frames. A video is generated comprising a series of displacement maps. The parameters of movement of the body structure are detected by analysis of the displacement maps. The image acquisition may detect the movement of the body structure without inducing such movement.

30 Claims, 25 Drawing Sheets
(24 of 25 Drawing Sheet(s) Filed in Color)

(56) References Cited

U.S. PATENT DOCUMENTS

| | | | |
|---|---|---|---|
| 5,606,971 A | 3/1997 | Sarvazyan | |
| 5,662,113 A | 9/1997 | Liu | |
| 5,752,515 A | 5/1998 | Jolesz et al. | |
| 5,810,731 A | 9/1998 | Sarvazyan et al. | |
| 5,840,028 A | 11/1998 | Chubachi et al. | |
| 6,026,173 A * | 2/2000 | Svenson et al. | 382/131 |
| 6,102,865 A | 8/2000 | Hossack et al. | |
| 6,106,465 A | 8/2000 | Napolitano et al. | |
| 6,152,878 A * | 11/2000 | Nachtomy et al. | 600/467 |
| 6,246,895 B1 | 6/2001 | Plewes | |
| 6,312,382 B1 | 11/2001 | Mucci et al. | |
| 6,413,216 B1 | 7/2002 | Cain et al. | |
| 6,425,867 B1 | 7/2002 | Vaezy et al. | |
| 6,491,636 B2 | 12/2002 | Chenal et al. | |
| 6,508,768 B1 | 1/2003 | Hall et al. | |
| 6,689,060 B2 | 2/2004 | Phelps et al. | |
| 6,701,341 B1 * | 3/2004 | Wu et al. | 709/200 |
| 6,770,033 B1 | 8/2004 | Fink et al. | |
| 6,875,176 B2 | 4/2005 | Mourad et al. | |
| 7,449,306 B2 | 11/2008 | Elson et al. | |
| 2002/0038086 A1 | 3/2002 | Hynynen et al. | |
| 2002/0095081 A1 | 7/2002 | Vilsmeier | |
| 2002/0169394 A1 | 11/2002 | Eppstein et al. | |
| 2002/0193784 A1 | 12/2002 | McHale et al. | |
| 2003/0097068 A1 * | 5/2003 | Hossack et al. | 600/443 |
| 2003/0171672 A1 | 9/2003 | Varghese et al. | |
| 2003/0220556 A1 | 11/2003 | Porat et al. | |
| 2004/0049134 A1 | 3/2004 | Tosaya et al. | |
| 2004/0054357 A1 | 3/2004 | O'Donnell | |
| 2004/0059224 A1 * | 3/2004 | Varghese et al. | 600/450 |
| 2004/0172081 A1 * | 9/2004 | Wang | 607/17 |
| 2004/0210135 A1 | 10/2004 | Hynynen et al. | |
| 2004/0236219 A1 | 11/2004 | Liu et al. | |
| 2004/0249580 A1 | 12/2004 | Pourcelot et al. | |
| 2005/0004466 A1 | 1/2005 | Hynynen et al. | |
| 2005/0059876 A1 | 3/2005 | Krishnan et al. | |
| 2005/0080336 A1 | 4/2005 | Byrd et al. | |
| 2005/0259864 A1 | 11/2005 | Dickinson et al. | |
| 2005/0267695 A1 | 12/2005 | German | |
| 2006/0058673 A1 | 3/2006 | Aase et al. | |
| 2006/0074315 A1 | 4/2006 | Liang et al. | |
| 2006/0173320 A1 | 8/2006 | Radulescu | |
| 2007/0049824 A1 | 3/2007 | Konofagou et al. | |
| 2007/0219447 A1 | 9/2007 | Kanai et al. | |
| 2007/0239001 A1 | 10/2007 | Mehi et al. | |
| 2007/0276242 A1 | 11/2007 | Konofagou | |
| 2007/0276245 A1 | 11/2007 | Konofagou | |
| 2008/0194957 A1 | 8/2008 | Hoctor et al. | |
| 2008/0285819 A1 | 11/2008 | Konofagou et al. | |

OTHER PUBLICATIONS

Brekke, S.; Tegnander, E.; Torp, H. G.; Eik-Nes, S. H.; "Tissue Doppler gated (TDOG) dynamic three-dimensional ultrasound imaging of the fetal heart," Ultrasound Obstet Gynecol 2004 vol. 24(2); pp. 192-198.

Wang, Shougang; Lee, Wei-Ning; Luo, Jianwen; Konofagou, Elisa E.; "A composite imaging technique for high frame-rate and full-view cardiovascular ultrasound and elasticity imaging," IEEE Transactions on Ultrasonics, Ferrorelectrics, and Frequency Control 2008 vol. 55(10); pp. 2221-2233.

Wang, Shougang; Lee, Wei-Ning; Luo, Jianwen; Konofagou, Elisa E.; "A composite imaging technique for high frame-rate and full-view cardiovascular ultrasound and elasticity imaging," IEEE International Ultrasonics Symposium, New York, NY, Oct. 28-31, 2007.

Kanai, H. Propagation of spontaneously actuated pulsive vibration in human heart wall and in vivo viscoelasticity estimation. Ieee T Ultrason Ferr (2005) 52(11): 1931-1942.

Bercoff, J., Tanter, M., and Fink, M. (2004). Supersonic shear imaging: A new technique for soft tissue elasticity mapping. *IEEE Transactions on Ultrasonics Ferroelectrics and Frequency Control* 51, 396-409.

McLaughlin, J., M. McNeill, B. Braun and P. D. McCormack. Piezoelectric sensor determination of arterial pulse wave velocity. Physiol Meas (2003) 24(3): 693-702.

Greenwald, S. E. Pulse pressure and arterial elasticity. Qjm-an International Journal of Medicine (2002) 95(2): 107-112.

Tanter, M., J. Bercoff, L. Sandrin and M. Fink. Ultrafast compound imaging for 2-D motion vector estimation: application to transient elastography. IEEE Trans Ultrason Ferroelectr Freq Control (2002) 49(10): 1363-74.

Kanai, H. and Y. Koiwa. Myocardial rapid velocity distribution. Ultrasound Med Biol (2001) 27(4): 481-498.

Rogers, W. J., Y. L. Hu, D. Coast, D. A. Vido, C. M. Kramer, R. E. Pyeritz and N. Reichek. Age-associated changes in regional aortic pulse wave velocity. J Am Coll Cardiol (2001) 38(4): 1123-9.

Declerck, J., T. S. Denney, C. Ozturk, W. O'Dell and E. R. McVeigh. Left ventricular motion reconstruction from planar tagged Mr images: a comparison. Phys Med Biol (2000) 45(6): 1611-1632.

Kanai, H., A. Umezawa and Y. Koiwa (2000). Transcutaneous measurement of frequency dispersion in the regional pulse wave velocity. IEEE Ultrasonics symposium.

Roth, B. J. (2000). Influence of a perfusing bath on the foot of the cardiac action potential. *Circulation Research* 86, E19-E22.

Sinkus, R., J. Lorenzen, D. Schrader, M. Lorenzen, M. Dargatz and D. Holz. High-resolution tensor MR elastography for breast tumour detection. Phys Med Biol (2000) 45(6): 1649-1664.

Wang, Y. X., M. Halks-Miller, R. Vergona, M. E. Sullivan, R. Fitch, C. Mallari, B. Martin-McNulty, V. da Cunha, A. Freay, G. M. Rubanyi and K. Kauser. Increased aortic stiffness assessed by pulse wave velocity in apolipoprotein E-deficient mice. Am J Physiol Heart Circ Physiol (2000) 278(2): H428-34.

Sandrin, L., S. Catheline, M. Tanter, X. Hennequin and M. Fink. Time-resolved pulsed elastography with ultrafast ultrasonic imaging. Ultrason Imaging (1999) 21(4): 259-72.

Cutnell, J. and W. Kenneth (1998). Physics, Fourth Edition. New York. Table of Contents.

Heimdal, A., A. Stoylen, H. Torp and T. Skjaerpe. Real-time strain rate imaging of the left ventricle by ultrasound. J Am Soc Echocardiog (1998) 11(11): 1013-1019.

Konofagou E.E. and Ophir, J., (1998) A New Elastographic Method for Estimation and Imaging of Lateral Strains, Corrected Axial Strains and Poison's Ratios in Tissues, *Ultrasound in Medicine and Biology* 24(8), 1183-1199.

Konofagou E.E., Kallel F. and Ophir J., (1998) Three-dimensional Motion estimation in Elastography, IEEE Proceedings of the Symposium of Ultrasonics, Ferroelectrics and Frequency Control in Sendai, Japan, 1745-1748.

Nichols, W. and M. F. O'Rourke (1998). Vascular impedance.In McDonald's: blood flow in arteries: theoretical, experimental and clinical principles. E. Arnold. London. Table of Contents.

Sarvazyan, A. P., O. V. Rudenko, S. D. Swanson, J. B. Fowlkes and S. Y. Emelianov. Shear wave elasticity imaging: A new ultrasonic technology of medical diagnostics. Ultrasound Med Biol (1998) 24(9): 1419-1435.

Spach, M. S., Heidlage, J. F., Dolber, P. C., and Barr, R. C. (1998). Extracellular discontinuities in cardiac muscle—Evidence for capillary effects on the action potential foot. *Circulation Research* 83, 1144-1164.

Brooks, D. H., and MacLeod, R. S. (1997). Electrical imaging of the heart. *Ieee Signal Processing Magazine* 14, 24-42.

Sutherland, G. R. Color Doppler Myocardial Imaging—Potential Applications in Acquired and Congenital Heart-Disease. Acta Paediatr (1995) 84: 40-48.

Walker, W. F. and G. E. Trahey. A Fundamental Limit on Delay Estimation Using Partially Correlated Speckle Signals. Ieee T Ultrason Ferr (1995) 42(2): 301-308.

Gupta, K. B., Ratcliffe, M. B., Fallert, M. A., Edmunds, L. H., and Bogen, D. K. (1994). Changes in Passive Mechanical Stiffness of Myocardial Tissue with Aneurysm Formation. *Circulation* 89, 2315-2326.

Fung, Y. C. (1993). Biomechanics—Mechanical Properties of Living Tissues. New York. Table of Contents.

(56) References Cited

OTHER PUBLICATIONS

Kanai, H., H. Satoh, K. Hirose and N. Chubachi. A New Method for Measuring Small Local Vibrations in the Heart Using Ultrasound. Ieee T Bio-Med Eng (1993) 40(12): 12331242.

Zerhouni, E. A., D. M. Parish, W. J. Rogers, A. Yang and E. P. Shapiro. Human heart: tagging with MR imaging—a method for noninvasive assessment of myocardial motion. Radiology (1988) 169(1): 59-63.

Bonnefous, O. and P. Pesque. Time domain formulation of pulse-Doppler ultrasound and blood velocity estimation by cross correlation. Ultrason Imaging (1986) 8(2): 73-85.

Avolio, A. P., S. G. Chen, R. P. Wang, C. L. Zhang, M. F. Li and M. F. O'Rourke. Effects of aging on changing arterial compliance and left ventricular load in a northern Chinese urban community. Circulation (1983) 68(1): 50-8.

Edwards, C. H., Rankin, J. S., Mchale, P. A., Ling, D., and Anderson, R. W. (1981). Effects of Ischemia on Left-Ventricular Regional Function in the Conscious Dog. *American Journal of Physiology* 240, H413-H420.

Henderson, A., Parmley, W. W., and Sonnenbl, E. (1971). Series Elasticity of Heart Muscle During Hypoxia. *Cardiovascular Research* 5, 10-14.

Konofagou E.E., D'Hooge J.D., Ophir, J Myocardial Elastography—Feasibility Study in Vivo. *Ultrasound Med & Biol.*, vol. 28, No. 4, pp. 475-482 (2002).

Luo J, Fujikura K., Homma S, Konofagou EE (Aug 2007). Myocardial elastography at both high temporal and spatial resolution for the detection of infarcts. *Ultrasound in Medicine & Biology* 33(8): 1206-23.

Chen, Q. et al. "Estimation of Displacement Vectors and Strain Tensors in Elastography Using Angular Insonifications." *IEEE Transactions on Medical Imaging*, vol. 23, No. 12, pp. 1479-1489 (Dec. 1, 2004).

Choi, J.J. et al., "Optimization of Blood-Brain Barrier Opening in Mice using Focused Ultrasound.", 2006 IEEE Ultrasounics Symposium [online], Jun. 2007.

Choi JJ, Wang S, Brown TR, Small SA, Duff KE and Konofagou EE, "Noninvasive and Transient Blood-Brain Barrier Opening in the Hippocampus of Alzheimer's Double Transgenic Mice Using Pulsed Focused Ultrasound", Ultrasonic Imaging, 189-200, 2008.

Choi JJ, Wang S, Tung Y-S, Baseri B, Morrison B 3rd, Konofagou EE. "Delivery of pharmacologically-relevant sized molecules through the ultrasound-induced blood-brain barrier opening in vivo.", Neuroscience, Chicago, IL, USA, Oct. 17-21. 2009.

Feshitan, J.A. et al., "Microbubble size isolation by differential centrifugation", Journal of Colloid and Interface Science 329 (2009) 316-324.

International Search Report for PCT/US07/019149 dated Feb. 29, 2008.

International Preliminary Report on Patentability for PCT/US07/019149 dated Mar. 3, 2009, including the Written Opinion of the International Searching Authority dated Feb. 29, 2008.

International Search Report for PCT/US06/061809 dated Oct. 4, 2007.

International Preliminary Report on Patentability for PCT/US06/061809 dated Jun. 11, 2008, including the Written Opinion of the International Searching Authority dated Oct. 4, 2007.

International Preliminary Report on Patentability for PCT/US06/018454 dated Nov. 14, 2007, including the Written Opinion of the International Searching Authority dated Aug. 9, 2007.

International Search Report for PCT/US05/037669 dated Jun. 13, 2006.

International Preliminary Report on Patentability for PCT/US05/37669 dated Apr. 17, 2007, including the Written Opinion of the International Searching Authority dated Jun. 13, 2006.

International Search Report for PCT/US05/037670 dated Nov. 22, 2006.

International Preliminary Report on Patentability for PCT/US05/037670 dated Apr. 17, 2007, including the Written Opinion of the International Searching Authority dated Nov. 22, 2006.

International Search Report and Written Opinion of the International Searching Authority for PCT/US09/052563 dated Oct. 8, 2009.

Konofagou E E et al. "Elastographic Imaging of the Strain Distribution at the Anterior Cruciate Ligament and ACL-Bone Insertions" *27th Annual International Conference of the Engineering in Medicine and Biology Society*, pp. 972-975 (Shanghai, China Sep. 1-4, 2005).

McDannold, N. et al., "Blood-Brain Barrier Disruption Induced by Focused Ultrasound and Circulating Preformed Microbubbles Appears to be Characterized by the Mechnical Index.", Ultrasound Med Biol. Jan. 2008, v. 34(5), pp. 834-840.

McNally, D. et al. "Computer Vision Elastography: Speckle Adaptive Motion Estimation for Elastography Using Ultrasound Sequences." *IEEE Transactions on Medical Imaging*, vol. 24, No. 6, pp. 755-766 (2005).

Qin, S. and Ferrara, K,W., "Acoustic response of compliable microvessels containing ultrasound contrast agents", Phys. Med. Biol. 51 (2006) 5065-5088.

Qin, S. and Ferrara, K.W.,"The Natural Frequency of Nonliner Oscillation of Ultrasound Contrast Agents in Microvessels", Ultrasound in Med. & Biol., vol. 33, No. 7, pp. 1140-1148, 2007.

Sassaroli, E. and Hynynen, K,, "Forced linear oscillations of microbubbles in blood capillaries", J. Acoust. Soc. Am. 115 (6), Jun. 2004.

Sassaroli, E. and Hynynen, K., "Resonance frequency of microbubbles in small blood vessels: a numerical study", Phys. Med. Biol. 50 (2005) 5293-5305.

Sassaroli, E. and Hynynen, K., "Cavitation Threshold of Microbubbles in Gel Tunnels by Focused Ultrasound", Ultrasound in Med. & Biol., vol. 33, No. 10, pp. 1651-1660, 2007.

Silva, G.A. Nanotechnology approaches to crossing the blood-brain barrier and drug delivery to the CNS, BMC Neruosci, 9(Suppl 3): S4, 2008.

Unger, E.C. et al., "Therapeutic Applications of Lipid-Coated Microbubbles." Advanced Drug Delivery Reviews. May 2004, vol. 56(9), pp. 1291-1314.

Yuh, EL, et. al. Delivery of Systemic Chemotherapeutic Agent to Tumors by Using Focused Ultrasound: Study in a Murine Model. Radiology, 234(2): 431-437, 2005.

Zheng, Y.P. et al. "High Resolution ultrasound elastomicroscopy imaging of soft tissues: system development and feasibility; Ultrasound elastomicroscopy." *Physics in Medicine and Biology*, vol. 49, No. 17, pp. 3925-3938 (Sep. 7, 2004).

U.S. Appl. No. 11/697,573, filed Apr. 6, 2007.
U.S. Appl. No. 11/697,579, filed Apr. 6, 2007.
U.S. Appl. No. 12/096,254, filed Nov. 26, 2008.
U.S. Appl. No. 11/899,004, filed Aug. 30, 2007.
U.S. Appl. No. 11/697,579; Nov. 17, 2009, Non-Final Rejection.
U.S. Appl. No. 11/697,579; Oct. 15, 2009, Response to Final Rejection.
U.S. Appl. No. 11/697,579; Jul. 15, 2009, Response to Final Rejection.
U.S. Appl. No. 11/697,579; Apr. 15, 2009, Final Rejection.
U.S. Appl. No. 11/697,579; Jan. 16, 2009, Response to Non-Final Rejection.
U.S. Appl. No. 11/697,579; Jul. 18, 2008, Non-Final Rejection.

Choi et al. et al. Brain region and microbubble-size dependence of the focused ultrasound-induced blood-brain barrier opening in mice in vivo. IEEE International Ultrasonics Symposium, Rome, ITA, Sep. 20-23, 2009.

Huang et al. Watershed Segmentation for Breast Tumor in 2-D Sonography, May 2004, Ultrasound in Medicine and Biology, pp. 625-632.

Chang et al. 3-D US Frame Positioning Using Speckle Decorrelation and Image Registration, Jun. 2003, Ultrasound in Medicine and Biology, pp. 801-812.

EPO Search Report & Opinion and Office Action for EP0684017.2 dated Dec. 7, 2009 & Mar. 8, 2010.

(56) References Cited

OTHER PUBLICATIONS

U.S. Appl. No. 11/697,573; Jun. 23, 2010, Non-Final Rejection.
U.S. Appl. No. 11/697,579; May 17, 2010, Response to Final Rejection.
U.S. Appl. No. 11/697,579; Aug. 6, 2010, Response to Office Action.
Epstein-Barash et al., "A microcomposite hydrogel for repeated on-demand ultrasound-triggered drug delivery," *Biomaterials*, Mar. 29, 2010, 31: pp. 5208-5217.
International Search Report and Written Opinion for International Application No. PCT/US12/34136.
International Search Report and Written Opinion for International Application No. PCT/US12/35685.

* cited by examiner

0ms

18ms

36ms
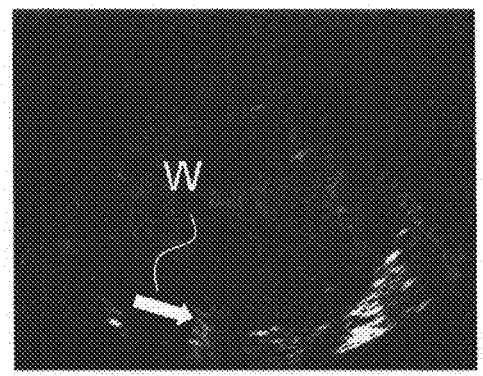 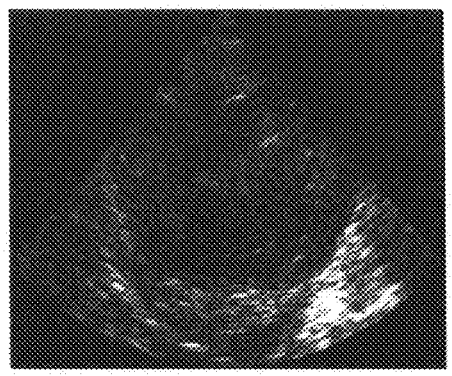
FIGURE 9(a)         FIGURE 9(b)
53ms
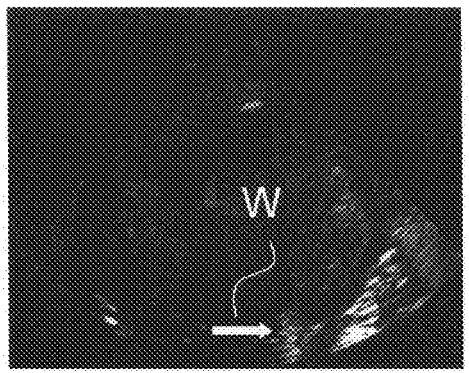 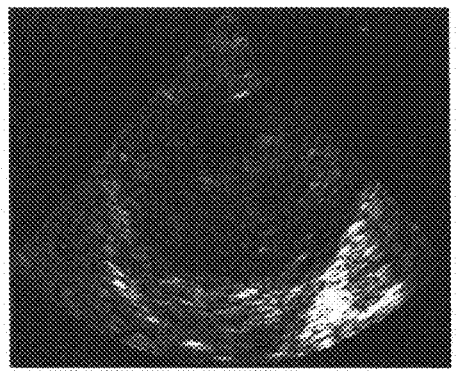
FIGURE 10(a)        FIGURE 10(b)

70ms
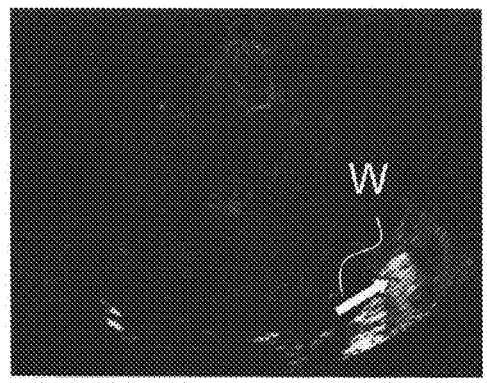
*FIGURE 11(a)*   *FIGURE 11(b)*

0ms

6ms

18ms

24ms

30ms

36ms

42ms

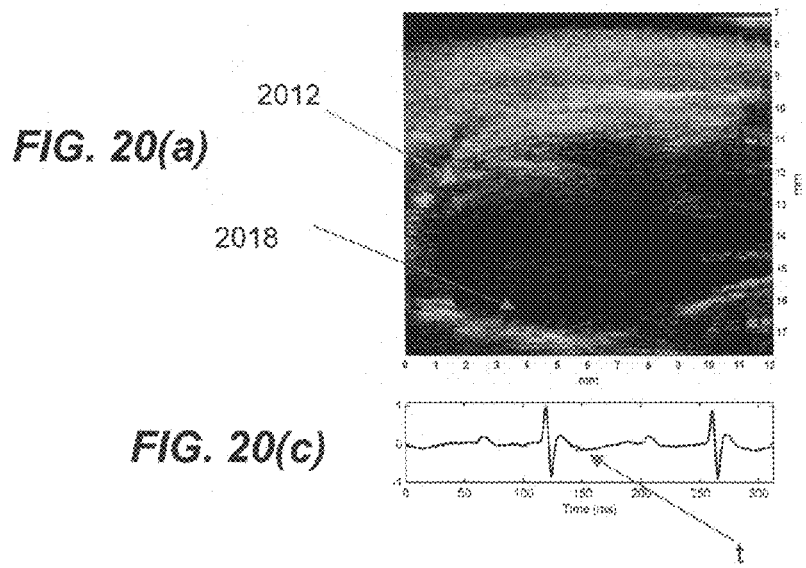
FIG. 20(a)
FIG. 20(c)
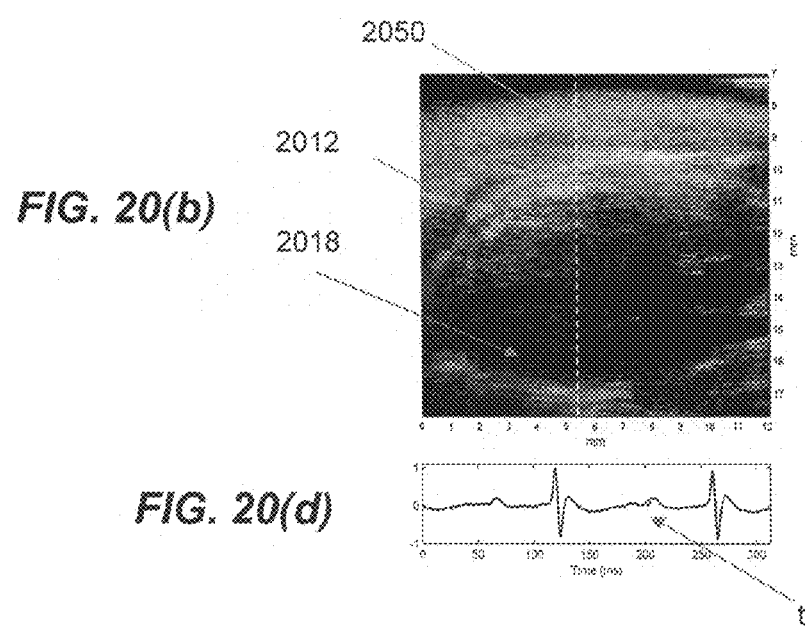
FIG. 20(b)
FIG. 20(d)

t=58.2ms t=58.8ms t t t=59.4ms t=60ms t t t=60.6ms t=61.2ms t t t=2.4ms t=5.2ms t=8ms t=10.8ms t=13.6ms t=16.4ms

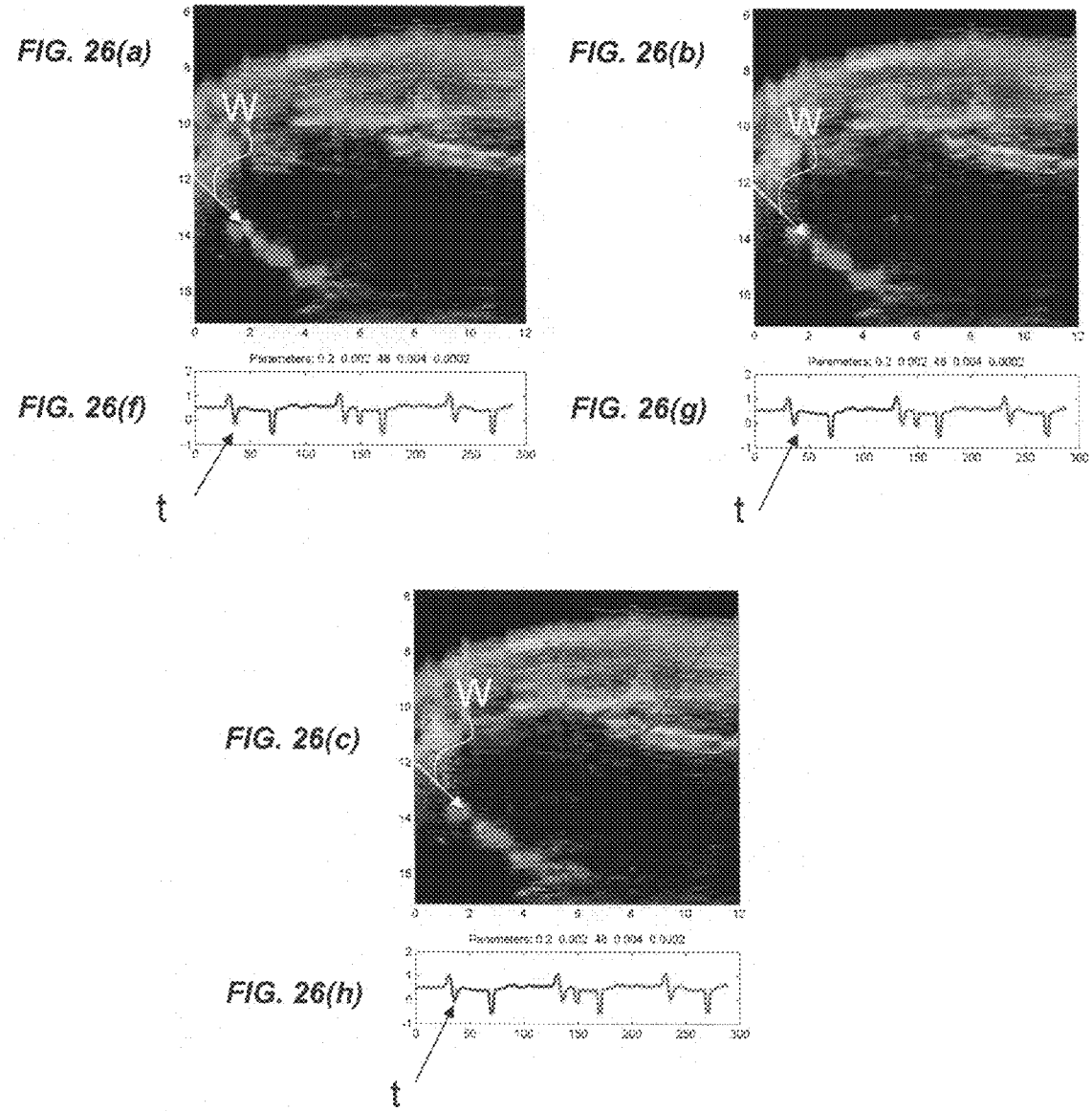

t=10.3ms t=11ms t=11.7ms t=12.4ms t=13.1ms t=13.8ms

SYSTEM AND METHOD FOR ELECTROMECHANICAL WAVE IMAGING OF BODY STRUCTURES

CROSS-REFERENCE TO RELATED APPLICATIONS

This application claims the benefit of U.S. Provisional Patent Application Ser. No. 60/680,081, filed on May 12, 2005, entitled "System and Method For Electromechanical Wave Imaging Of Body Structures," which is hereby incorporated by reference in its entirety herein A portion of the disclosure of this patent document contains material which is subject to copyright protection. The copyright owner has no objection to the facsimile reproduction by anyone of any portion of the patent document, as it appears in any patent granted from the present application or in the Patent and Trademark Office file or records available to the public, but otherwise reserves all copyright rights whatsoever.

A computer program listing is submitted in duplicate on CD. Each CD contains several routines which are listed in the Appendix. The CD was created on May 12, 2006. The files on the CD are incorporated by reference in their entirety herein.

BACKGROUND OF THE INVENTION

1. Field of the Invention

This invention relates to an imaging technique and system for detecting the propagation of mechanical waves within a body structure of a patient.

2. Background

Certain medical conditions, such as diagnosis of myocardial ischemia, are often difficult to establish in their early stages when treatment is most effective. Patients suffering from myocardial ischemia may present to an emergency room or acute care facility with typical cardiac symptoms such as chest pain, described as tightness, pressure, or squeezing, but some patients may have other symptoms such as arm or chin pain, nausea, sweating, or abdominal pain. Standard techniques such as electrocardiogram often provide inconclusive findings regarding ischemia, and sometimes may even be unable to identify situations in which ischemia has progressed to cell damage and myocardial infarction (MI). More reliable techniques are available for diagnosing infarction relative to its predecessor, ischemia. For example, a blood test to measure the creatine kinase-MB (CK-MB) enzyme level is used for detection of myocardial cell damage. Other useful serum markers include troponin I, and to a lesser extent, myoglobin. However, the blood levels of these compounds may take several hours to rise, so that diagnosis of MI may be delayed. Reliance on blood tests alone may result in a significant loss of time when early aggressive therapy is warranted.

Less invasive diagnostic techniques have become available through the observation of mechanical properties of tissue via imaging techniques. Such evaluation of the function of the heart, cardiovascular tissue, or other body structures is based on the mechanical interpretation of the movement of the these structures, such as, for example, the active contractions and passive relaxation of the myocardium. For example, U.S. Pat. No. 5,542,298 to Sarvazyan et al. describes a technique and apparatus for determining the physical state parameters of a medium by generating oscillations in a reference medium.

Using current imaging techniques, the evaluation of the heart function is mainly based on a single mechanical interpretation of myocardial deformation. In order to quantify these deformations, several techniques have been introduced, such as tissue doppler imaging (Sutherland et al., 1995), strain rate imaging (Heimdal et al., 1998), and myocardial elastography (Konofagou et al., 2002) in the field of ultrasound imaging, and cardiac tagging (Declerck et al., 2000) in the field of magnetic resonance imaging. By use of these techniques, the deformations of the myocardium are quantified over a complete cardiac cycle in order to provide some information on the myocardial viability.

Low frequency mechanical vibrations in the heart were shown by Kanai et al. (Kanai and Koiwa, 2001; Kanai et al., 1993), in human patients. They developed a new ultrasound system to demonstrate that several pulsive mechanical vibrations were obtained around end-systole and end-diastole in the frequency range of 25 to 100 Hz. U.S. Pat. No. 5,840,028 to Chubachi, Kania and Koiwa describes their ultrasonic imaging equipment for the measurement of small vibrations in myocardial tissues. The apparatus and technique described in the '028 patent have several drawbacks, including requiring the use of complicated ultrasound systems that may not be clinically applicable.

Accordingly, there is a need in the art for a diagnostic tool for determining characteristics of body structures which avoids the drawbacks of the prior art.

SUMMARY

The present invention relates to an elasticity imaging technique which is able to evaluate mechanical wave propagation, and to provide an estimation of electrical propagation in a noninvasive manner. It is based, at least in part, on the discovery that in the context of certain diseased or affected tissue, an electromechanical wave was observed, through sequential images, to travel faster than normal tissue. Accordingly, the present invention provides an imaging method for detecting such conditions, such as, for example, myocardial ischemia. It is a further object of the invention to detect anomalies in body function by observation of such wave characteristics.

These and other objects of the invention, which will become apparent with reference to the disclosure herein, are accomplished by a system and method for detecting wave propagation within the tissue of a patient in a series of image frames representing movement of such tissue of the body structure. Image data is acquired comprising a series of image frames corresponding to the movement of the tissue. In an exemplary embodiment of the invention, the tissue may be the wave propagation in the myocardium. In another exemplary embodiment, the movement of body tissue may be wave propagation in the arteries or the aorta.

A correlation calculation is performed on the image frames to generate a matrix with the location of correlation maxima representing the relative displacement between the first and second image frames, also referred to as a displacement map. A video is generated comprising a series of displacement maps. The parameters of movement of the cardiac structure are detected, such as velocity, attenuation, frequency, etc. The wave may be a shear wave, representative of the electrical wave propagation within the body structure.

In accordance with the invention, the objects as described above have been met, and the need in the art for a technique which overcomes the deficiencies in the prior art has been satisfied. For example, the technique of detecting and measuring contractile movement of the heart, for example, provides near instantaneous results, which can be used by the physician in the emergency room or acute care setting.

BRIEF DESCRIPTION OF THE DRAWINGS

Further objects, features and advantages of the invention will become apparent from the following detailed description taken in conjunction with the accompanying figures showing illustrative embodiments of the invention, in which:

FIGS. 7(a)-11(b) are images illustrating the propagation of a wave within a body structure in accordance with an exemplary embodiment of the present invention.

FIG. 20(a) is an axial displacement map overlaid to the grayscale B-mode image of the left ventricle during systole in accordance with the present invention.

FIG. 20(b) is an axial displacement map overlaid to the grayscale B-mode image of the left ventricle during diastole (relaxation phase) in accordance with the present invention.

FIG. 20(c) is an ECG indicating the time of the acquisition during the cardiac cycle of FIG. 20(a) in accordance with the present invention.

FIG. 20(d) is an ECG indicating the time of the acquisition during the cardiac cycle of FIG. 20(b) in accordance with the present invention.

FIGS. 26(a)-(e) illustrate a sequence of axial displacement maps overlaid to the grayscale image (0.12 ms between successive frames) indicating an electromechanical wave propagating in the posterior wall of the mouse from the apex towards the base during pacing in the right atrium close to the sinoatrial node in accordance with the present invention.

FIGS. 26(f)-(j) illustrate the ECG signal plotted below each respective image of FIGS. 26(a)-(e) indicating the time t of the acquisition during the cardiac cycle in accordance with the present invention.

Figure 1:
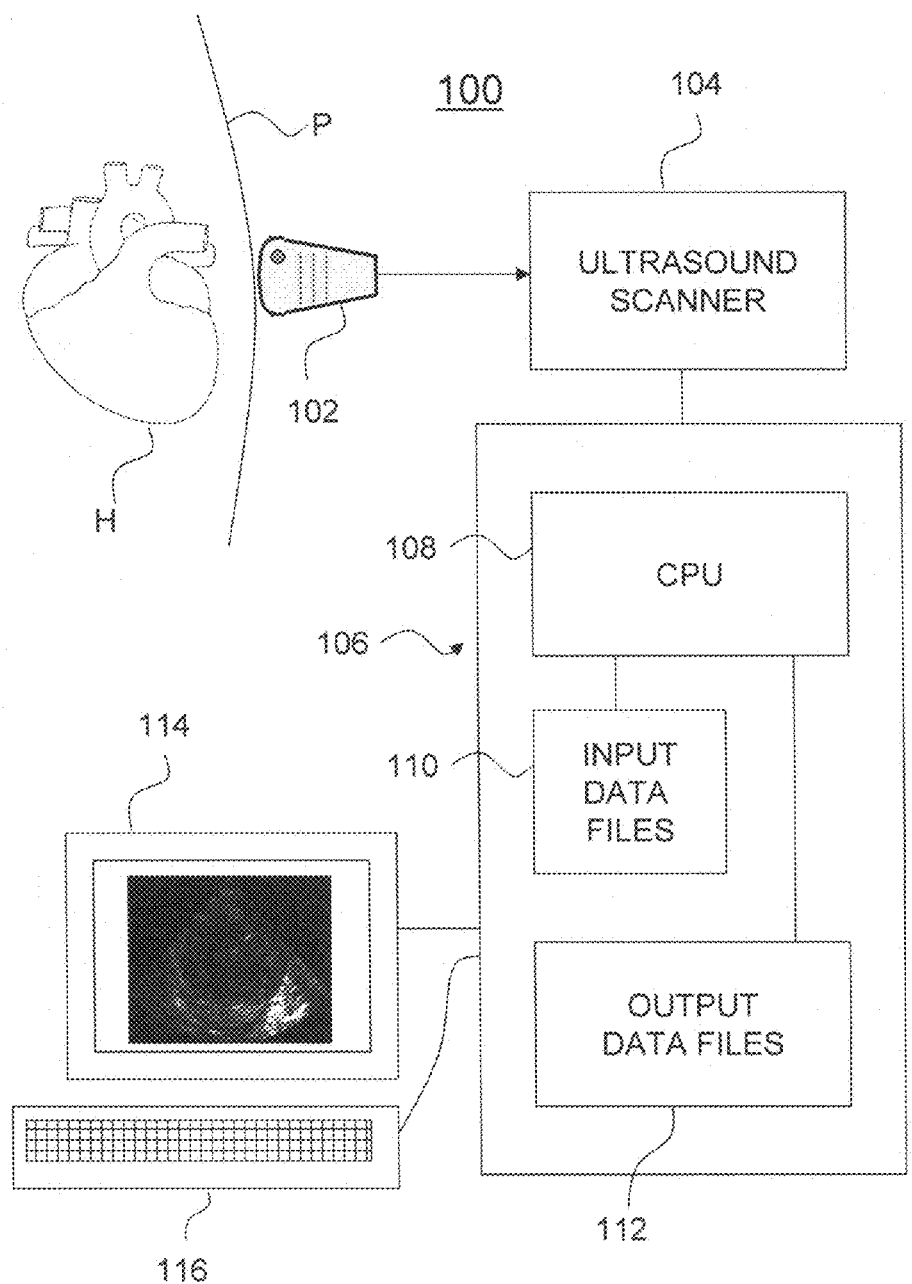
FIG. 1 is a diagram illustrating the system in accordance with the present invention.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments.

DETAILED DESCRIPTION OF EXEMPLARY EMBODIMENTS

This invention will be further understood in view of the following detailed description of exemplary embodiments of the present invention.

The system and methods described herein are useful for analyzing data obtained by an image generating device, such as an ultrasound transducer. The systems and methods are also useful for measuring mechanical properties and estimating the electrical characteristics of a body tissue structure or organ, such as, for example, the myocardium or the aorta.

For example, the invention may be used in connection with imaging and characterizing the propagation of electromechanical waves in the heart. During the cardiac cycle, electrical waves propagate in the myocardium in order to induce its contraction. Contraction of the myocardial fibers results in a strong mechanical wave, which, since it results from the coupling of the electrical excitation and the mechanical properties of the myocardium, is referred to herein as an "electromechanical wave." The speed of this wave is a function of the electrical and mechanical properties of the myocardium, and, according to the invention, can be used to detect changes in these properties to diagnose heart diseases.

An exemplary embodiment of the system is illustrated in FIG. 1 and designated system 100. System 100 may include an image detection device, such as ultrasound probe 102, which is used to create images of the heart H or other organ or structure of the patient P. The image detection device does not induce discernible vibration in the body structure, and merely detects pre-existing motion. The signals detected by the probe 102 may be transferred to an ultrasound scanner 104. The exemplary embodiments described herein are designed to work with conventional ultrasound scanners. For example, commercial portable scanners, such as Terason 2000, high frequency scanners, such as Visualsonics Vevo 770, and routinely used clinical scanners, such as GE System Five or GE Vivid Five or Seven, are useful for image acquisition in accordance with the exemplary embodiments. The raw data produced by the scanner 104 may be transferred to a computer 106 having a CPU 108 for processing the data. In the exemplary embodiment, the computer and CPU would be Dell PC with a 2 GHz processor. It is understood that the computer and CPU may also be integrated with the ultrasound scanner 104. Also useful in the system would be storage such as disk drives, for storing data on input files 110 and for writing output onto output files 112. As will be described herein, input files 110 may include information such as thresholds. Output files 112 may include the displacement maps, videos of myocardium displacements, or computed data, such as electromechanical wave properties. It is understood that a preprogrammed chip may be used to execute the algorithms described herein. Typically, an output device, such as monitor 114, and an input device, such as keyboard 116, are also components of the system.

Figure 2:
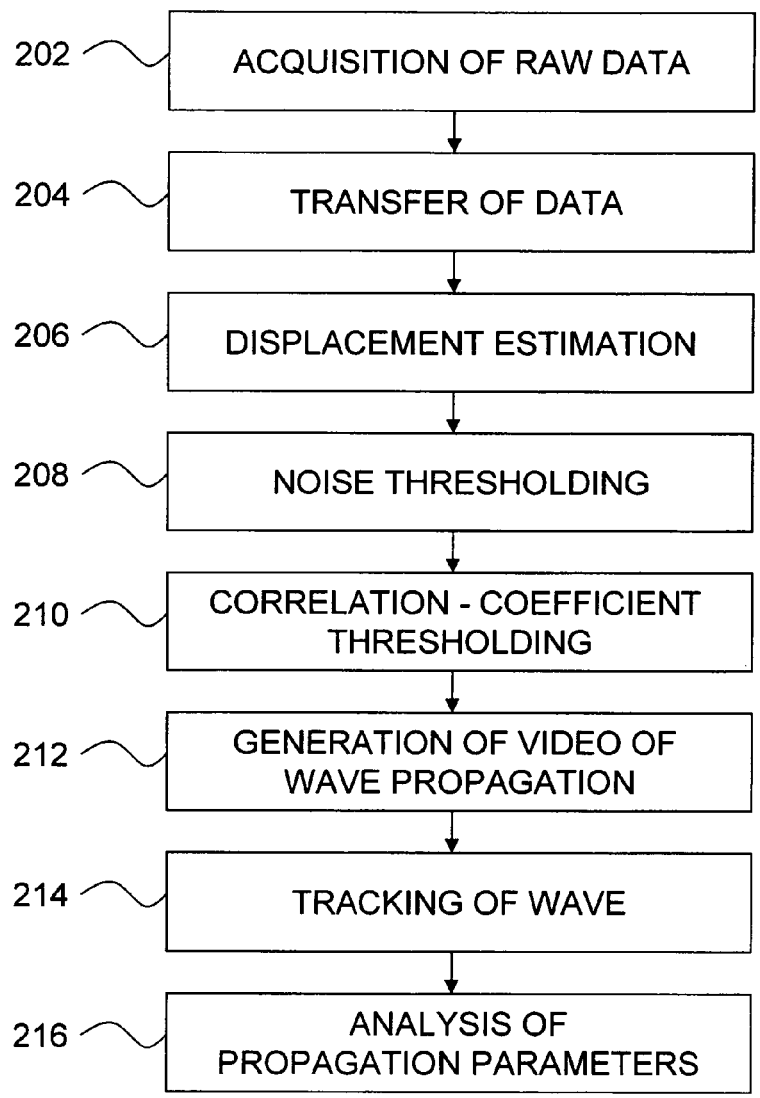
FIG. 2 is a diagram illustrating exemplary stages in a method in accordance with the present invention.

In accordance with an exemplary embodiment, the methods described herein are particularly useful for imaging the propagation of electromechanical waves in the heart. A method for detecting the properties of the electromechanical wave are described herein and represented in FIG. 2. In an early stage in the procedure, raw imaging data of the body structure is acquired by image acquisition equipment such as the ultrasound probe 102 and scanner 104. In the exemplary embodiment, a set of N frames of raw ultrasound data of the heart is acquired during a cardiac cycle at high frame rate, e.g., higher than 100 fps, although frame rates of about 56 fps and 170 fps, etc., yield useful results (step 202). The selected frame rate should be commensurate with the speed of the propagation of the movement, such at the wave, being studied. The electrocardiogram (EKG) may also be recorded. The raw data may be digitized and stored in real-time in the scanner memory.

In a subsequent stage, the data may be transferred to a computer for processing (step 204). In an exemplary embodiment, the transfer may occur using a protocol such as ethernet TCP IP. This step is optional, as the computer may be integrated with the scanner 104.

At step 206, the raw data received from the image acquisition equipment is processed. In the exemplary embodiment, the data processing step computes an estimation of the displacement of particular objects in the images, such as the myocardium, between consecutive frames. Typically this processing step occurs off-line; however, it is understood that this procedure may occur sequentially subsequent to receiving two consecutive frames. According to the exemplary embodiment, axial displacements (in the direction of the transducer) are computed. Lateral, or elevational, displacements (perpendicular to the transducer) may also be computed using a similar technique (Konofagou and Ophir 1998; Konofagou et al. 1998).

N−1 displacement 2D maps (also referred to as correlation matrices) are computed through the correlation of two consecutive frames i and i+1 ($1 \leq i \leq N-1$). Each frame is represented by a matrix of pixel values. The displacement maps provide an indication of the local axial movements between frames. Estimation of the axial displacements from the two consecutive frames is performed using a speckle tracking algorithm. In this algorithm, the time-shifts in the backscattered signals are determined between two consecutive frames through cross-correlation of small sliding windows over the entire ultrasound image. For each window, the signal of the frame i and the frame i+1 are cross-correlated. The maximum of the correlation coefficient gives an estimation of the time-shift between the two signals. This time-shift may be converted to a spatial displacement by assuming a constant speed of sound for the tissue. This technique may detect displacements on the order of 10 μm. Using small correlation windows of 7.5 mm, the resolution of the displacement maps is in the millimeter range. The cross-correlation algorithm suitable for estimating displacement between consecutive image frames is described in U.S. Provisional Patent Application No. 60/619,247, filed Oct. 15, 2004, which is incorporated by reference herein. In the exemplary embodiment, a matlab program Multiframe (see Appendix) is used to compute the displacement maps for the complete sequence of frames obtained at step 202, above. Multiframe calls the matlab routine FunCalculDispl (see Appendix) to compute the displacements for the sequence of frames. FunCalculDispl in turn calls the routine Correlation2D.cpp (see Appendix) which is a C program that computes the displacement map between consecutive frames. As discussed above, Correlation2D.cpp uses small sliding windows to find the displacement which maximizes the correlation coefficient for each part of the image. In accordance with other embodiments of the invention, auto-correlation calculations or coherence calculations, as are known in the art, may be performed.

Two optional threshold steps may be executed in the procedure 200. Step 208 is the application of a threshold on the energy of the signal, in order to remove the noise that is below a predetermined signal-to-noise ratio. Typically, low energy ultrasound signals (e.g., noise in the cavity of the heart) may be removed from the displacement map according to this method. Step 210 is the application of a threshold on the correlation coefficient to remove erroneous estimates in the displacements. In the exemplary embodiment, the noise threshold and correlation-coefficient threshold may be implemented within the routine Correlation2D.cpp. The levels of the thresholds are determined experimentally and may be stored in an input data file 110 for processing on the CPU 108.

Steps 206, 208 and 210 are illustrated sequentially; however, it is understood that these steps may occur simultaneously or any other order to appropriately process the data. Moreover, one or more of these steps may be omitted from the process described herein.

As another step in the procedure, a video of the sequence of N−1 displacement maps may be assembled to create a video of the displacements of the body structure or tissue (step 212). In the exemplary embodiment, a video of the myocardium displacements is created by this technique.

The video of the displacement map of the myocardium will depict the propagation of the electromechanical wave. A next step in the procedure may be observation and tracking of the wave propagation (step 214). Although such tracking may be done manually, it may be difficult to discern the wave by visual observation and thus make accurate measurements. Accordingly, wave tracking may be performed by an algorithm, such as TrackPositionWave (see Appendix), a matlab program which locates the position of the wave front by performing a zero-crossing calculation on consecutive displacement maps.

Figure 3:
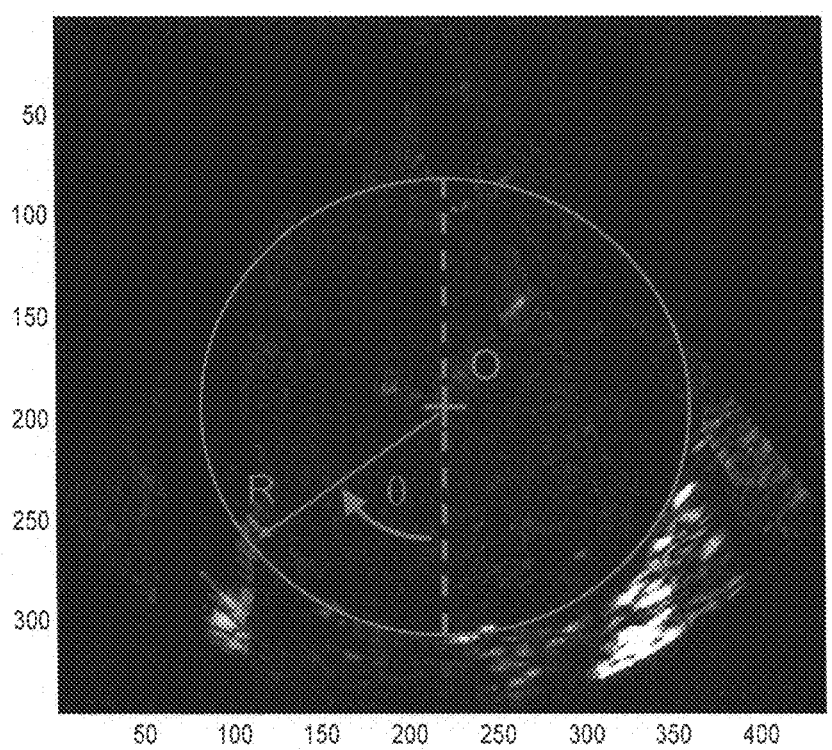
FIG. 3 is a diagram illustrating a technique for measuring movement of structures within an image in accordance with the present invention.
Figure 4:
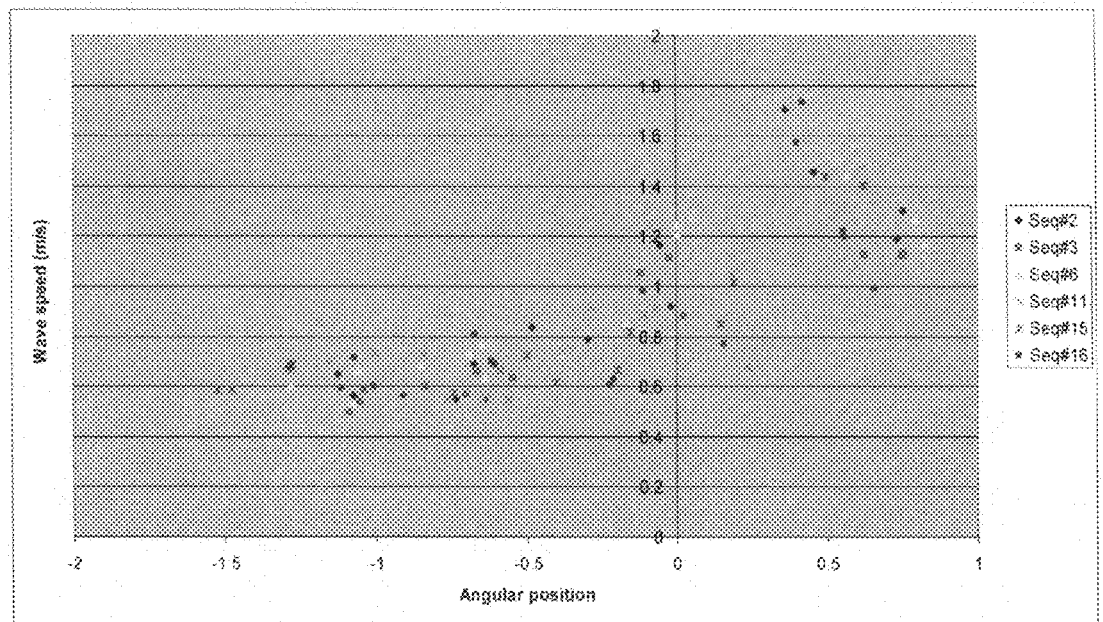
FIG. 4 is a chart representing the velocity of structures within an image in accordance with the present invention.

The parameters of the electromechanical wave, e.g., velocity, amplitude, attenuation, frequency, etc., may be analyzed at step 216. For example, the velocity of the electromechanical wave may be computed as a function of its position in the myocardium. As illustrated in FIG. 3, the wall of the myocardium is approximated as circular with a radius R, and the origin of the spherical coordinate system was chosen at the center of the cavity. The wavefront of the electromechanical wave was then tracked by its angular coordinate θ. The matlab function Overlay (see Appendix) may be used to compute the transformation of the raw image into polar coordinates. This routine may also display the displacement map superimposed on the ultrasound grayscale data. As an example, the speed of the electromechanical wave is shown on the FIG. 4 as a function of the angular position.

Figure 5:
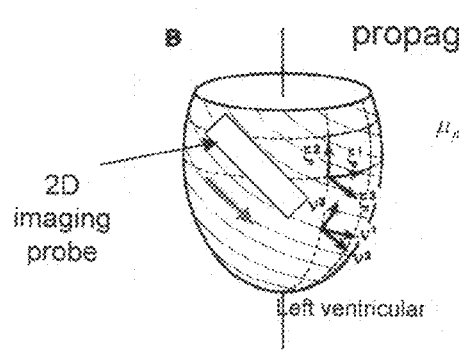
FIG. 5 illustrates a technique of detecting wave propagation in accordance with a further embodiment of the present invention.
Figure 6:
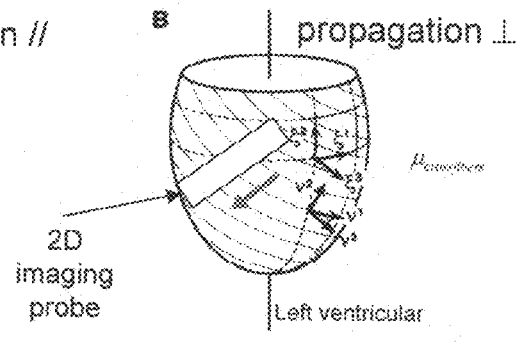
FIG. 6 illustrates a technique of detecting wave propagation in accordance with yet another embodiment of the present invention.
Figure 7A:
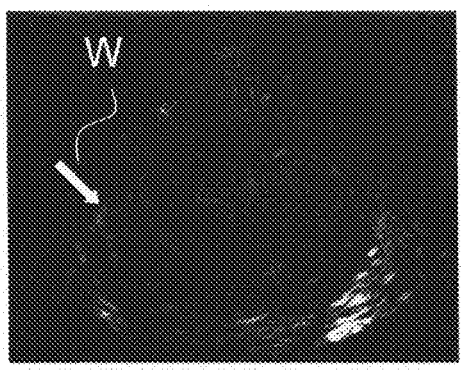
Figure 7B:
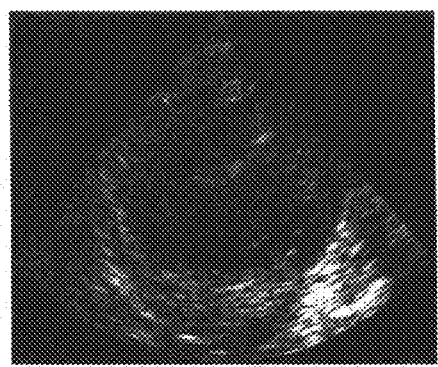
Figure 8A:
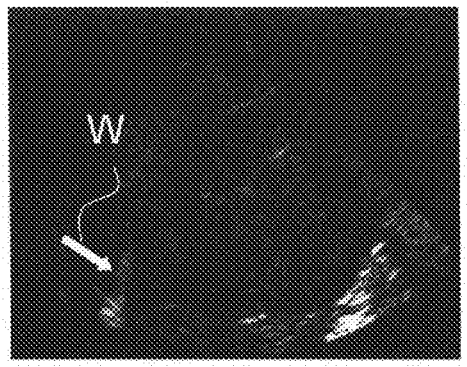
Figure 8B:
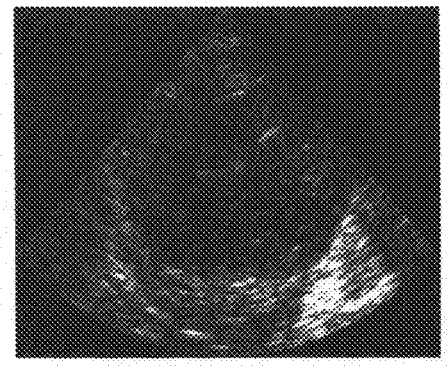
Figure 12A:
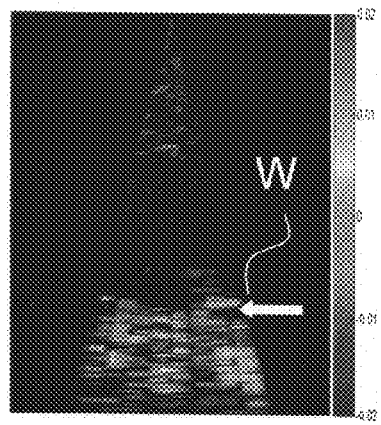
FIGS. 12(a)-18(b) are images illustrating the propagation of a wave within a body structure in accordance with another exemplary embodiment of the present invention.
Figure 12B:
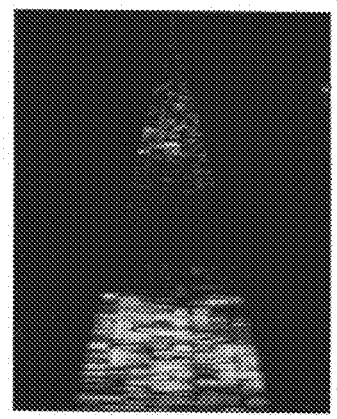
Figure 13A:
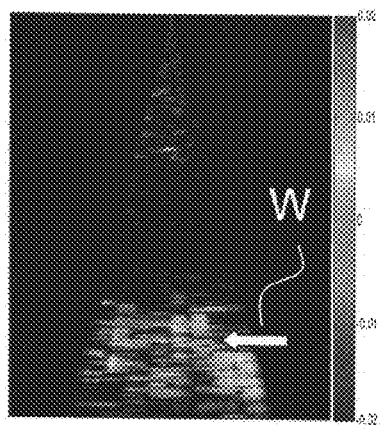
Figure 13B:
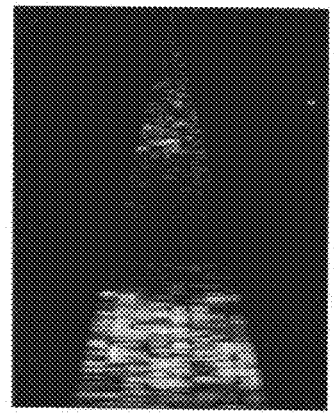
Figure 14A:
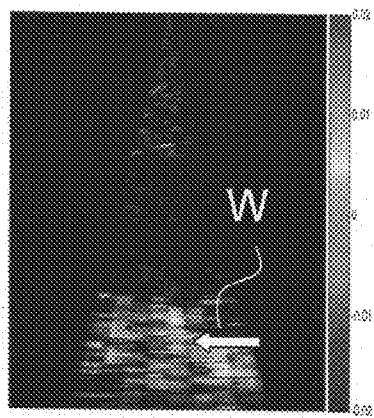
Figure 14B:
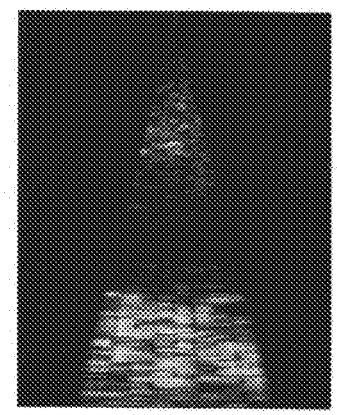
Figure 15A:
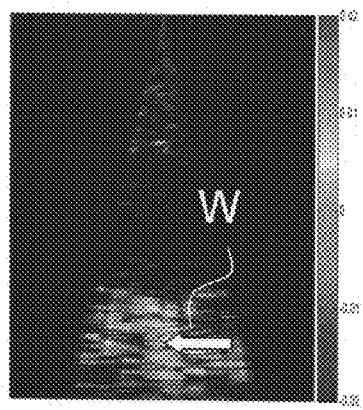
Figure 15B:
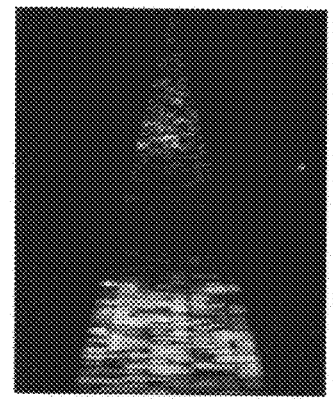
Figure 16A:
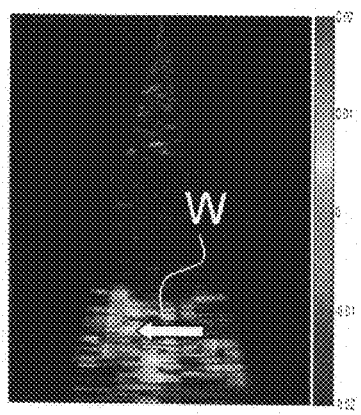
Figure 16B:
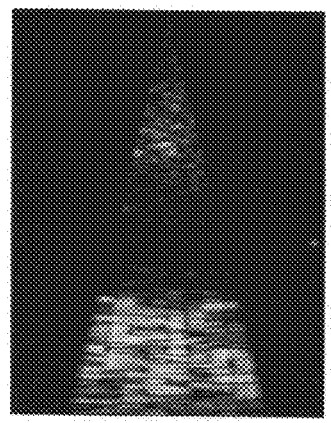
Figure 17A:
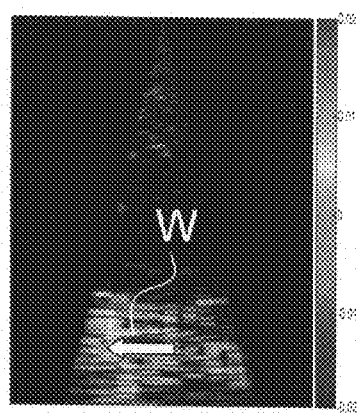
Figure 17B:
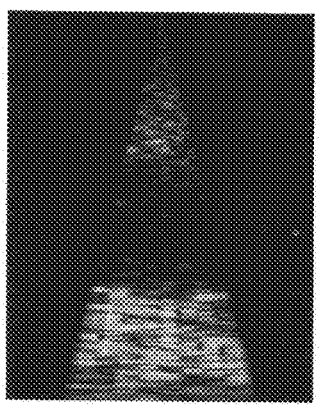
Figure 18A:
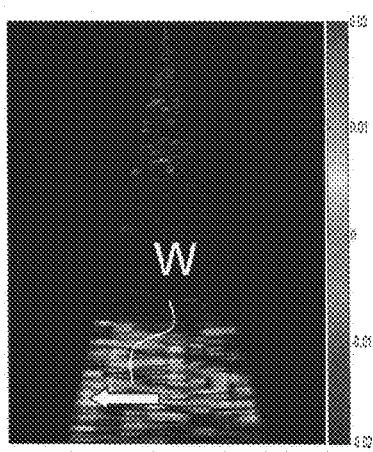
Figure 18B:
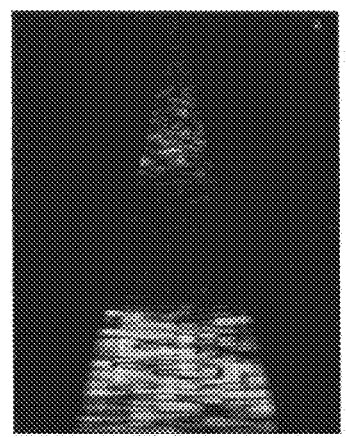

The ultrasound imaging method described herein has the advantage of being completely non-invasive. In an exemplary embodiment, the system described herein may be implemented in real-time on commercial scanners. It has been shown that the electrical conductivity is transversely isotropic with respect to fiber direction, with a longitudinal velocity of about 0.6 m/s and a transverse velocity of about 0.2 m/s (Roth, 2000; Spach et al., 1998). The electromechanical wave velocity noted herein was very close to the longitudinal velocity of the mechanical wave. The transverse velocity may be measured by using ultrasound imaging and displacement estimation using a 3D imaging probe or a rotational 2D imaging probe. FIG. 5 illustrates a transducer setup for 2D imaging of the longitudinal waves, and FIG. 6 illustrates a transducer setup for 2D imaging of transverse waves.

The mechanical component of the electromechanical wave is related to the viscoelastic properties of the soft tissue. The elastic properties of the myocardium have been widely investigated. It has been shown that the stiffness of the myocardium increases during ischemia and recovers after reperfusion (Edwards et al., 1981; Gupta et al., 1994; Henderson et al., 1971). Thus, early detection of cardiovascular diseases such as ischemia and infarction can be strongly improved through non invasive characterization of the local myocardial elasticity.

Low frequency shear (mechanical) waves propagate in soft tissue at low velocity (0.5 to 50 m/s). For an isotropic and infinite medium, it has been shown (Bercoff et al., 2004; Sarvazyan et al., 1998) that the velocity of the shear wave is related to the shear modulus μ and the density ρ by:

$$V_S = \sqrt{\frac{\mu}{\rho}}$$

According to another exemplary embodiment of the invention, a system may be implemented to provide early detection of ischemia through the measure of the velocity of the mechanical wave.

However, the myocardium has also anisotropic mechanical properties and can be considered as a transverse isotropic medium. As a consequence, two shear waves of different velocities can propagate in the myocardium. Fast mechanical (shear) waves propagate in the direction of the fibers, and slow mechanical (shear) waves propagate in the direction perpendicular to the fibers. The measure of the two wave velocities can be achieved by using 3D Ultrasound imaging systems or multiple acquisitions of 2D images with a rotation of the transducer (see FIGS. 5-6). The wave velocities are related to two elastic constants, $\mu_{//}$ the shear modulus in direction of the fibers and $\mu_\perp$ the cross-fiber shear modulus.

$$V_{//} = \sqrt{\frac{\mu_{//}}{\rho}} \quad (2)$$

$$V_\perp = \sqrt{\frac{\mu_\perp}{\rho}} \quad (3)$$

The systems and methods described herein can potentially have different applications in the field of early detection of cardiovascular diseases and cardiac imaging.

For example, the measure of the electrical excitation propagation is of high interest in cardiology for early detection of heart diseases but also for pacing the heart when heartbeat is too slow or irregular. The purpose of an artificial pacemaker is to stimulate the heart when either the heart's natural pacemaker is not fast enough or if there are blocks in the electrical conduction system preventing the propagation of electrical impulses. Thus, in order to implant the artificial pacemaker at the correct location, the electrical propagation must be determined accurately. To date, in vivo imaging of the electrical propagation in the heart requires implanting an electrode matrix (up to 500 electrodes) to measure extracellular potentials at the surface of the heart (Brooks and MacLeod, 1997). This highly invasive and potentially precarious surgical procedure cannot be performed on human patients for diagnostic purposes. The present invention provides a means for determining electrical propagation in the myocardium of a subject, in the context of achieving an effective position of a pacemaker in the subject. Other methods known in the art involve optically-based techniques which also require invasive procedures, such as open-chest surgery.

The present invention may be further used to create images and thereby detect myocardial ischemia in a subject either having symptoms (e.g., chest, arm, or chin pain, nausea, shortness of breath, and/or sweating) or a subject subjectively lacking such symptoms (e.g., "silent ischemia"), whereby a finding of increased electromechanical wave velocity (relative to control values) in a region of the myocardium of a subject is consistent with and supportive of a diagnosis of myocardial ischemia in that region. The present invention may also be used to diagnose, or assist in surgical intervention in, (i) conduction disturbances, such as re-entry phenomena, or associated with pharmaceutical agents, such as antidepressants or hyperkalemia, (ii) arrythmias and dysrhythmias (e.g., surgical treatment of ventricular dysrhythmias, diagnosis of low-amplitude atrial fibrillation); and (iii) tissue abnormalities associated with cardiomyopathies or trauma, etc.

EXAMPLE A

Imaging of Canine Heart

The procedure described hereinabove was performed in an anesthetized open-chested dog. The transducer was placed on the anterior wall of the left ventricle of the heart, to obtain a short axis view. Approximately every two minutes, a sequence of three cardiac cycles was acquired during the experiment, with a frame rate of 56 fps. The 2D displacement maps were estimated using the cross-correlation method (window size: 5 mm, 90% overlap). The axial displacements were processed for the different sequences. On the displacement video, two electromechanical waves were clearly detected, propagating in the posterior wall of the left ventricular, from the septum (left side of the images) to the lateral wall (right side). The propagation of the mechanical wave corresponds to the electrical activity shown on an associated EKG.

The first electromechanical wave is found at the end-diastolic phase of the cardiac cycle (which corresponds to the beginning of the contraction). FIGS. 5(a) through 9(a) show five consecutive frames of the propagation of the wave. The location of the electromechanical wavefront is indicated by arrow W in each of FIGS. 7(a)-11(a). The displacements maps are overlaid to the grayscale ultrasound images (see, FIGS. 7(b)-11(b)). Blue displacements are in the direction of the transducer (top of the image), and red displacements are in the opposite direction. As shown in these images, the contraction of the myocardium starts on the left side (septum) and propagates to the right side of the image. In the figures, the blue region appears on the left side of the images (behind the wavefront), and the red region appears on the right side of the image (in front of the wavefront). The maximum displacements shown are 75 µm (dark blue and dark red), and the wave propagates within a few milliseconds. Therefore it is impossible to visually detect this electromechanical wave on the grayscale images. The wave speeds as measured using the techniques described above are represented in FIG. 4. The wave velocity was found to be approximately 0.6 m/s in the posterior wall, which was corroborated by invasive electrophysiological measurements using a matrix of electrodes. Temporary regional ischemia was then induced by coronary artery ligation. The velocity of the electromechanical wave was found to increase up to approximately 1.7 m/s in the ischemic region. Although not entirely understood, this strong increase is believed to be due to an increase of the shear modulus in the ischemic region or a change in the conduction velocity, or both. (A second electromechanical wave has also been detected at the end-systole phase. However, due to its high propagation speed (related to the high contraction of the myocardium), the propagation was not caught with a sufficiently high frame rate. Some evidences of its propagation are detected in the human experiments, described herein.)

EXAMPLE B

Imaging of Human Heart

The procedure 200 described hereinabove was performed on a young healthy patient. The transducer was placed on the patient's thorax in order to image the heart in the short axis view. A sequence of approximately four cardiac cycles was acquired at a very high frame rate of 170 fps using a Vingmed System Five for RF image acquisition. In order to reach such a high frame rate, only a small part of the heart (the left ventricle) was imaged (80×40 mm). The axial displacements were processed for each frame. On the displacement video, 2 electromechanical waves were clearly seen, propagating in the posterior wall of the left ventricular (not shown). FIGS. 12(a)-18(a), which are consecutive displacement maps superimposed on the grayscale images (FIGS. 12(b)-18(b)), illustrate the propagation of the electromechanical wave at the end-systole phase. The speed was found to be 0.65 m/s in the posterior wall. The location of the electromechanical wavefront is indicated by arrow W in each of FIGS. 12(a)-18(a).

EXAMPLE C

Imaging of Cardiovascular Tissue in Mice

Animal Preparation

The procedure described hereinabove was performed on anesthetized mice. The mice were anesthetized with tribromoethanol. The hair was removed using potassium thioglycolate and the mouse was placed in the supine position on a heating stage (VisualSonics, Toronto ON, Canada) in order to keep the body temperature steady. ECG signal was obtained from the extremities. The ultrasound probe was placed on the chest or the abdominal wall using degassed ultrasound gel (Aquasonic 100, Parker Laboratories Inc., Fairfield N.J., USA) as a coupling medium.

RF Signal Acquisition

An ultrasound scanner specifically developed for imaging small animals (Vevo 770, Visualsonics, Toronto ON, Canada) was used in this exemplary embodiment. The high frequency ultrasound probe was composed of a single focused transducer working at 30 MHz, with a focal depth of 12.7 mm. The transducer was mechanically rotated and real-time 2D images could be acquired at a frame rate of up to 60 Hz. The field of view was 12×12 mm, the axial resolution was 50 microns, and the lateral resolution was 100 microns.

A digitizer (2 channels, 200 MS/s, 14 bits, CS14200, Gage Applied Technologies, Lachine QC, Canada) mounted on a PC computer slot was connected to the analog RF-output of the ultrasound scanner. In addition, two TTL outputs were used to trigger the digitizer on the 2D frames. This setup allows the real-time acquisition of more than one thousand 2D RF-data, e.g., images.

In the exemplary embodiment, the ultrasound probe was placed on the chest in the parasternal position to obtain a longitudinal (long-axis) view of the left ventricle of the heart. The probe could also be positioned over the abdomen to obtain a longitudinal view of the abdominal aorta.

High Frame Rate Acquisition

In addition to the real-time scanning mode, a high frame rate acquisition mode (EKV) was provided on the scanner in the exemplary embodiment in order to allow detailed visualization of the heart contraction. The equipment operate as quickly as 8000 frames per minute, although the user may see 1000 frames per minute due to dropped calls. Using this technique, the ultrasound acquisition of each RF-line was triggered on the mouse ECG. The transducer was slowly rotated and for each position of the transducer, ultrasound echo signals were recorded with a pulse repetition frequency (PRF) of 8000 pulses/s during several cardiac cycles. The ECG was simultaneously recorded and thus allowed for the synchronization of the RF-lines based on the R-wave peak, a reliable peak of the ECG during the cardiac cycle. The complete acquisition duration was approximately 5 min.

To compute the tissue motion, RF-signals and ECG signals were digitized during the EKV acquisition and transferred to the computer in real-time. The data were then processed off-line, RF-lines were synchronized using the R-wave peak of the ECG signal, and a complete set of 2D ultrasound RF-data was reconstructed at 8000 fps for one complete cardiac cycle (approximately 150 ms).

Motion Estimation

The motion of the tissue was estimated off-line using a classical speckle tracking algorithm (Bonnefous and Pesque 1986). This technique was based on detecting the small local displacements of the tissue that occur between two consecutive frames. With the current method, only axial displacements (in the direction of the transducer) were computed. In this algorithm, the time-shifts in the backscatterered signals were determined between the two consecutive frames through cross-correlation of small sliding windows over the entire ultrasound image. This technique allowed the detection of very small displacements on the order of 1 μm or less (correlation windows of 150 μm, overlapping 90%). Finally, the movie of the axial displacements was processed at a frame rate up to 8000 frame/s for the entire cardiac cycle. It is understood tha lateral displacement may be obtained using the same technique.

Frequency Analysis

The axial displacements were analyzed in the frequency domain as a function of the time. A sliding Blackman window (100 points, 25 ms) as is known in the art, was moved along the displacement variation at a fixed depth, in steps of 2 ms. The windowed signals were zero-padded to 8192 points and their FFT was calculated. The frequency content of the displacements was evaluated graphically by plotting these spectra as a function of time. Based on this frequency analysis, the transient and the slow motions of the tissues were separated using a digital filter. The displacement estimates were temporally filtered using an FIR band-pass filter with cut-frequencies of $f_1=50$ Hz and $f_2=500$ Hz, which allows the removal of the low frequency components but also the high frequency noise.

Wave Velocity

To analyze the propagation of the mechanical waves, the phase velocity of the vibration was determined for an angular frequency ω. The wave was assumed to propagate with a velocity c in a direction r that was arbitrarily determined on the image by the direction of the wall, and a set of measurement points was selected on this direction. The wave number is k=ω/c, and the phase of the wave is φ(r)=kr along the direction of propagation. The phase was measured as a function of the propagation distance r, using the Fourier Transform of the temporal displacements at the location r computed at the angular frequency ω. Finally, the derivative of the phase of the wave with respect to distance was estimated using a linear regression fit on the set of measurements points, and the velocity of the wave at the frequency f was calculated:

$$c(f)=2\pi f/(\partial \phi/\partial r) \qquad (4)$$

Modulus Estimation

The theory of elastic wave propagation in soft biological tissue was considered in order to derive the Young's modulus of the tissue. Assuming that the medium is infinite and isotropic, the speed of shear waves propagation could be derived from general equations of the dynamic theory of elasticity (Landau and Liftshitz 1965). However, it is understood that the propagation of elastic waves in the myocardium may optionally take into account additional characteristics such as the active properties of the muscle fibers, the strong anisotropy of the tissue, and/or the geometry of the ventricles.

For the transverse wave on the artery wall, a simple model of the propagation of a pressure wave in a viscoelastic infinite thin conduit filled with an incompressible fluid is well described by the Moens-Korteweg equation (Korteweg 1879; Moens 1879):

$$c = \sqrt{\frac{Eh}{2R\rho}} \qquad (5)$$

where c is the velocity of the wave, E is the Young's modulus of the conduit wall, h is the wall thickness, ρ is the density of the fluid and R the radius of the tube. According to this equation, the elasticity of the vessel wall can be derived from the measurement of the pulse wave velocity in the artery.

Results of Example C

In Vivo Cardiac Imaging

Figure 19:
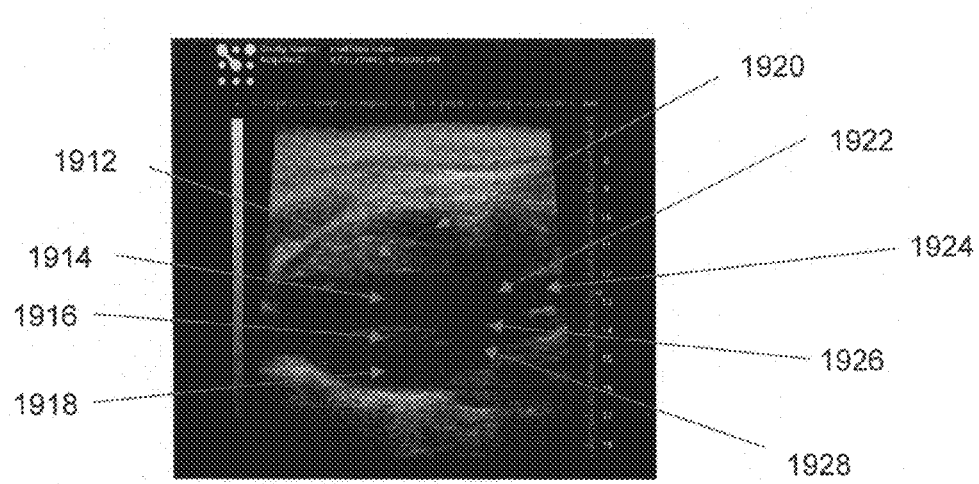
FIG. 19 is an ultrasound image of a mouse left ventricle in a parasternal long-axis view.

FIG. 19 shows a B-mode image 1910 of a typical parasternal long-axis view obtained in a normal mouse. Image 1910 shows the main structures of the left ventricle: the intraventricular septum 1912, the cavity of the left ventricle 1914, the papillary muscle inside the cavity 1916 and the posterior wall 1918 which is visible due to strong reflections at the epicardium-lung interface. Also shown in image 1910 is the right ventricle 1920, aortic valve 1922, aorta 1924, mitral valve 1926, and left atrium 1928. In this embodiment, the duration of the average cardiac cycle was 138 ms. Axial displacements were estimated for the complete set of data. In order to keep the displacements at optimal magnitudes for the estimation (on the order of 1 μm (Walker and Trahey 1995)) and to reduce the amount of data, the number of frames was halved, which also reduced the frame rate to 4000 fps.

FIGS. 20(a) and 20(b) show the color-coded axial displacements overlaid onto the grayscale B-mode image for two different phases of the cardiac cycle. During the systolic phase, the contraction of the myocardium is shown by positive displacements (red region) of the posterior wall 2018 and negative displacements of the septum 2012 (blue region) (FIG. 20(a)). In the diastolic phase, the directions of the displacements of the posterior wall 2018 and the septum 2012 (and the colors associated with the direction of movement) are reversed during the relaxation (FIG. 20(b)). It should be noted that even if a large part of the myocardium of the posterior wall is not visible, the motion of the epicardium undergoes similar motion. The time of acquisition of FIG. 20(a) is indicated at point t of FIG. 20(c). The time of acquisition of FIG. 20(b) is indicated at point t of FIG. 20(d).

Figure 21A:
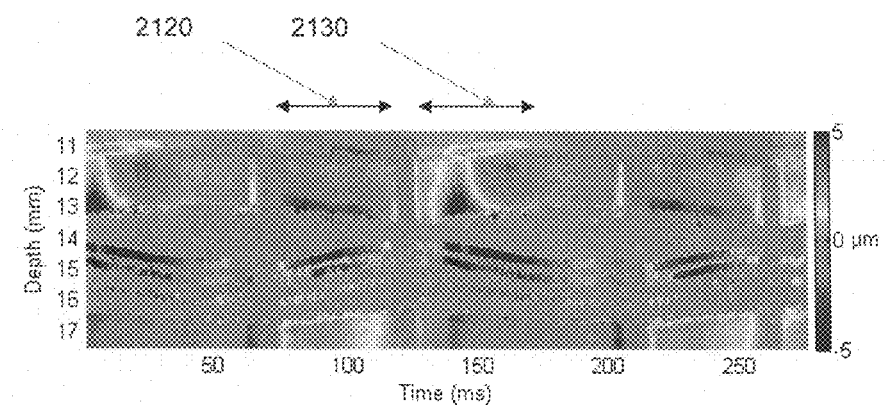
FIG. 21(a) is a time plot illustrating the temporal variation of the axial displacements estimated on one central RF-line as line plotted on FIG. 20(b) in accordance with the present invention.

A temporal analysis of the motion was performed for single RF lines of the image. The axial displacement along one central line of the image (indicated by the white, dotted vertical line 2050 on FIG. 20(b)) is shown as a function of time in FIG. 21(a) with the corresponding ECG signal (FIG. 21(d)). (FIGS. 2(a)-(d) are aligned on a temporal basis.) On this line 2050, the displacements of the septum, the papillary muscle and the posterior wall are shown in a M-mode format over two cardiac cycles. It shows the successive main phases of the cardiac cycle: the contraction of the myocardium (systole) indicated by arrow 2120 initiated at the R-wave peak of the ECG, followed by the relaxation phase (diastole) indicated by arrow 2130. The duration of the active contraction was approximately 50 ms, and that of the relaxation 35 ms. In addition to this slow and large motion, some rapid transient variations of a few ms were observed at the beginning and at the end of the systolic phase, in the septum and the posterior wall.

Figure 21B:
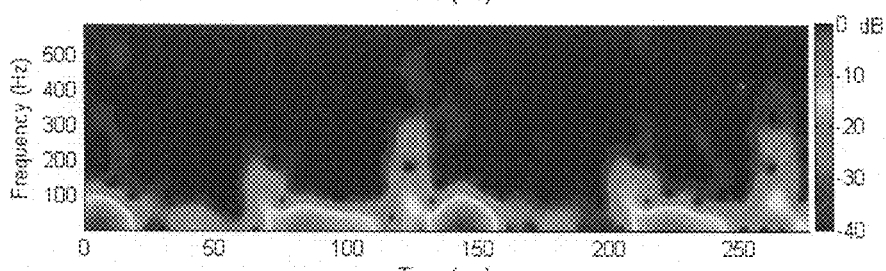
FIG. 21(b) illustrates the frequency content of the displacement variation in the septum at the depth of 12.5 mm plotted as a function of time in accordance with the present invention.

In order to separate the elecromechanical wave from other mechanical waves generated by vibrations resulting from valve functions or blood flow, high-pass filtering was performed. The frequency content of the tissue displacements resulting from vibrations in the septum (at depth of 12.5 mm) was analyzed as a function of time and is shown in FIG. 21(b). During the contraction and the relaxation of the heart, the motion of tissue was found to be in the low frequency range of up to 60 Hz. However, during the transient motion at the end of systole, much larger frequency components were found that ranged between 50 Hz and 500 Hz. The same effect was found for the transient motion at the beginning of systole, but the frequency range was limited between 50 Hz and 250 Hz. Thus, it was possible to almost completely separate the transient part of the displacement by filtering out the low frequency component of the motion. After filtering the displacements using a FIR band-pass filter with cut-off frequencies $f_1$=50 Hz and $f_2$=500 Hz, the two vibrations were clearly visible and are shown on FIG. 21(c) as regions 2150 and 2152. These rapid variations occurred within less than 3 ms around the beginning of systole and end-systole.

End of Systole

Figure 22A:
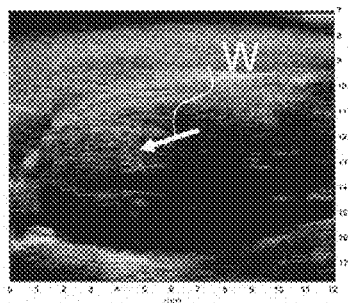
FIGS. 22(a)-(d) illustrate a sequence of axial displacement maps overlaid to the grayscale B-mode image of the left ventricle around end-systole taken every 0.6 ms showing the propagation of a first mechanical wave front in the septum in accordance with the present invention. The arrows indicate the progression of the wave front in the septum.
Figure 22B:
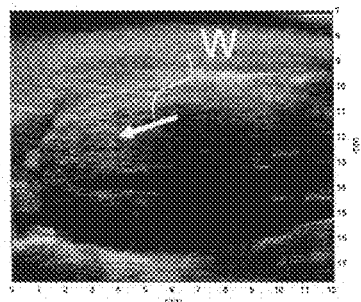
Figure 22G:
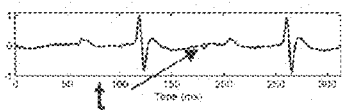
FIGS. 22(g)-(l) illustrate the ECG signal plotted below each respective image of FIGS. 22(a)-(f) indicating the time t of the acquisition during the cardiac cycle in accordance with the present invention.
Figure 22H:
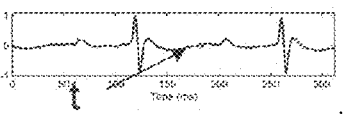
Figure 22C:
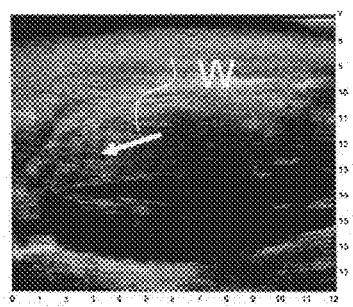
Figure 22D:
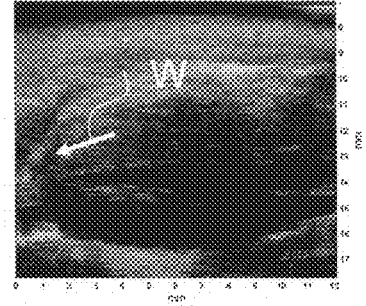
Figure 22I:
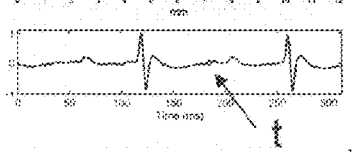
Figure 22J:
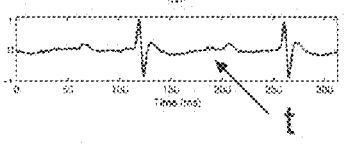
Figure 22E:
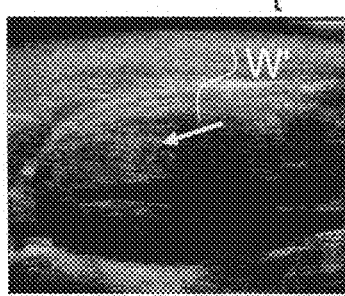
FIGS. 22(e)-(f) illustrate a sequence of axial displacement maps overlaid to the grayscale B-mode image of the left ventricle around end-systole taken every 0.6 ms showing the propagation of a second mechanical wave front in the septum in accordance with the present invention. The arrows indicate the progression of the wave front in the septum.
Figure 22F:
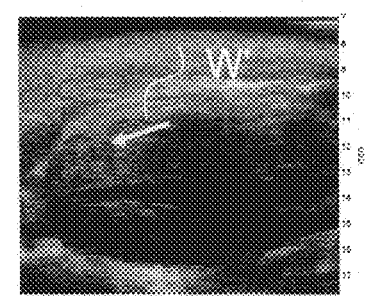
Figure 22K:
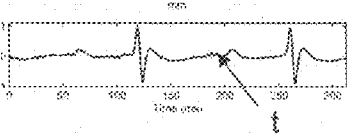
Figure 22L:
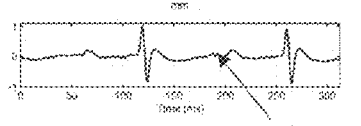

In order to analyze spatially the vibration around end-systole, we considered the data between 52 ms and 70 ms after the peak of the R-wave. FIGS. 22(a)-(d) show a sequence of axial displacements overlaid onto the grayscale B-mode images every 0.6 ms around end-systole. This sequence uncovers a strong mechanical wave W propagating in the longitudinal direction of the ventricle along the myocardium, from the base (right side of the images) to the apex (left side). In other words, as the tissue locally vibrates along the axial direction of the beam (i.e., along the beam axis), a transverse wave propagates along the lateral direction (i.e., in-plane, perpendicular to the beam axis). A second wave W' is shown in FIGS. 22(e)-(f).

Figure 21C:
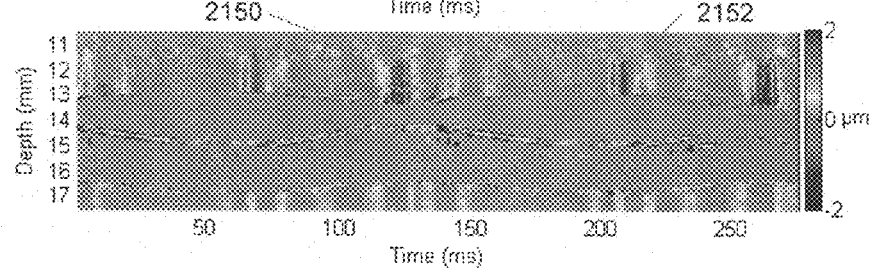
FIG. 21(c) is a time plot illustrating the temporal variation of the axial displacements after bandpass filtering of the plot illustrated in FIG. 21(a) showing the transient and high frequency components in accordance with the present invention.
Figure 21D:
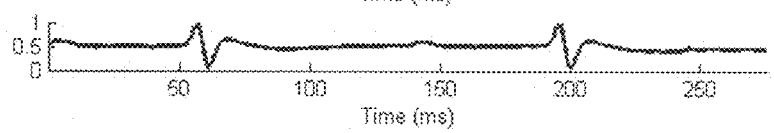
FIG. 21(d) illustrates the ECG signal acquired simultaneously with the data illustrated in FIGS. 21(a)-(c) in accordance with the present invention.
Figure 23:
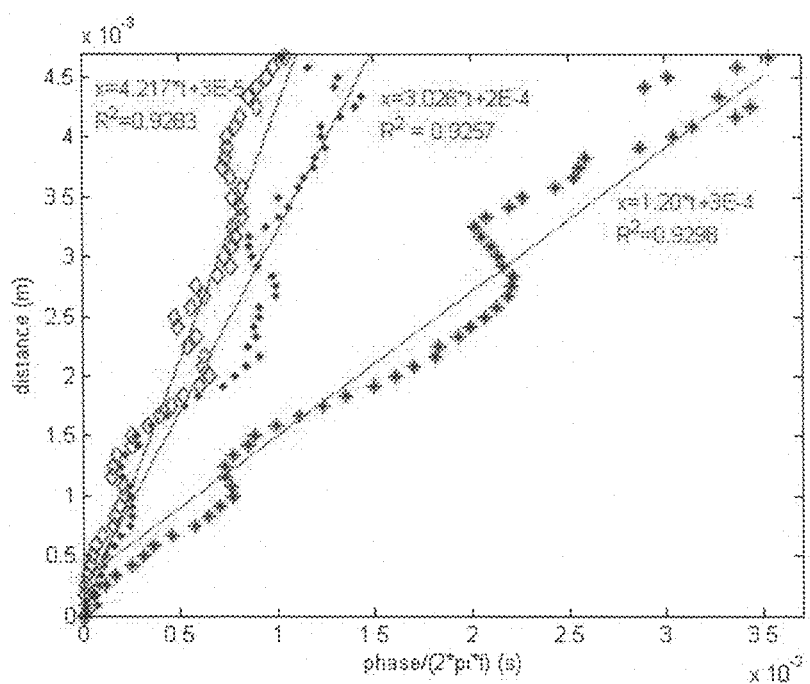
FIG. 23 is a plot illustrating the distance of propagation as a function of the phase of the end-systolic wave at three frequencies in accordance with the present invention.
Figure 24A:
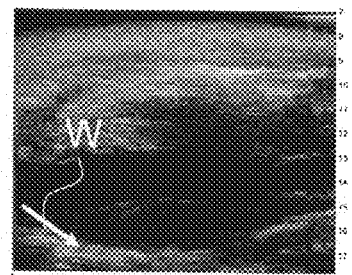
FIGS. 24(a)-(f) illustrate a sequence of axial displacement maps overlaid to the grayscale B-mode image of the left ventricle around the beginning of systole taken every 2.8 ms, showing the propagation of a strong mechanical wave in the posterior wall in accordance with the present invention. The arrows indicate the progression of the wave front in the posterior wall.
Figure 24B:
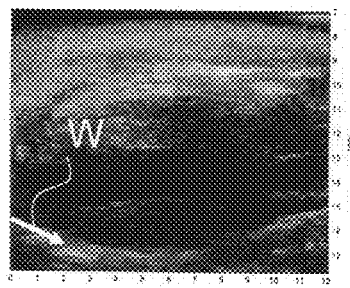
Figure 24G:
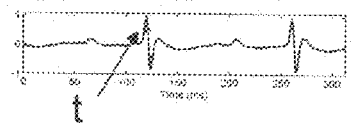
FIGS. 24(g)-(l) illustrate the ECG signal plotted below each respective image of FIGS. 24(a)-(f) indicating the time t of the acquisition during the cardiac cycle in accordance with the present invention.
Figure 24H:
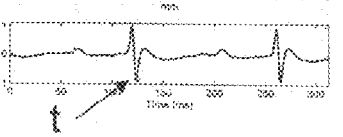
Figure 24C:
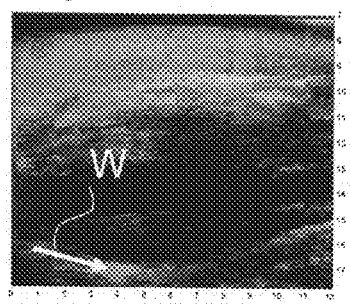
Figure 24D:
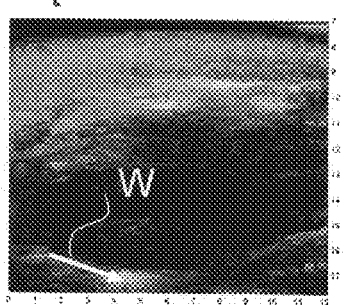
Figure 24I:
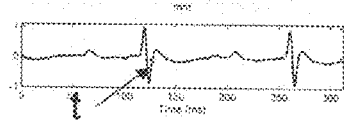
Figure 24J:
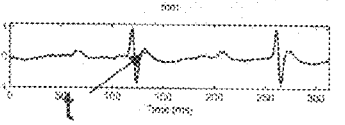
Figure 24E:
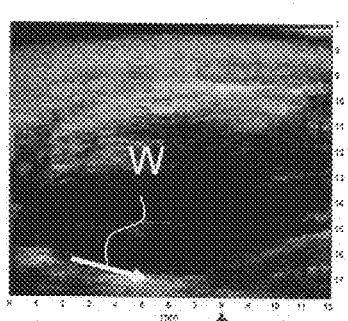
Figure 24F:
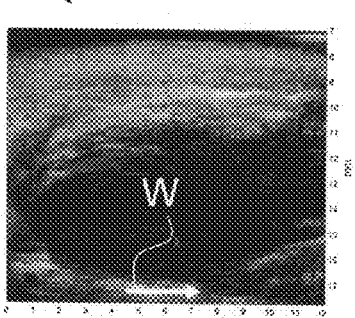
Figure 24K:
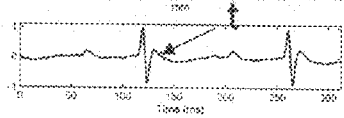
Figure 24L:
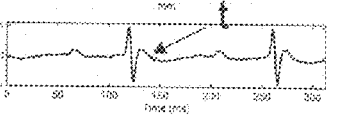

The mechanical wave, i.e., generated by localized vibrations in the muscle (FIG. 21(c)), was visible both in the posterior wall and the septum. Its amplitude was found to be eight times higher in the septum. Only the mechanical wave propagating in the septum is described herein. A set of 60 samples was selected in the septum along the propagation direction (lateral direction of the image), and the phase of the wave was computed at different frequencies. Three frequencies were selected for which the displacement amplitude was large enough to detect, e.g. with respect to noise level: (*) 82 Hz (●) 246 Hz (◇) 410 Hz. The phase velocity of the wave was computed for these frequencies and a large dispersion was found. The distance of propagation was plotted in FIG. 23 as a function of the phase of the wave divided by the angular frequency. The phase velocity was found to be 1.20 m/s at 82 Hz, 3.02 m/s at 246 Hz and 4.21 m/s at 410 Hz.

Beginning of Systole

The same analysis was performed at the beginning of systole. The filtered data were processed between 0 ms and 20 ms from the peak of the R-wave. FIGS. 24(a)-(f) show a sequence of axial displacements overlaid to the grayscale B-mode images every 2.8 ms around the beginning of systole. A strong vibration was found in the septum, but no wave propagation was visible in the image plane. Therefore, a mechanical wave may propagate in the perpendicular direction, but was not be observed with the equipment described herein.

Figure 25:
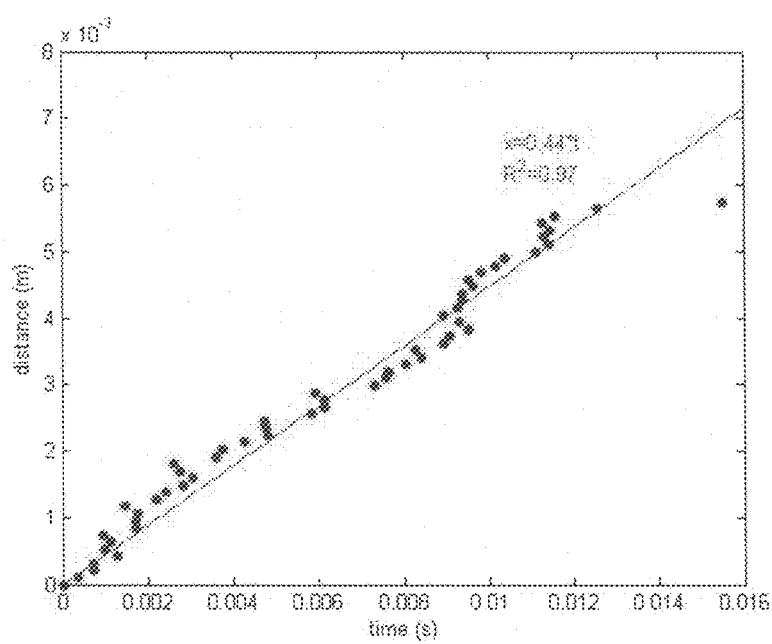
FIG. 25 is a plot illustrating the distance of propagation as a function of the phase of the wave at the frequency of 80 Hz during the beginning of systole transient motion in accordance with the present invention.
Figure 26D:
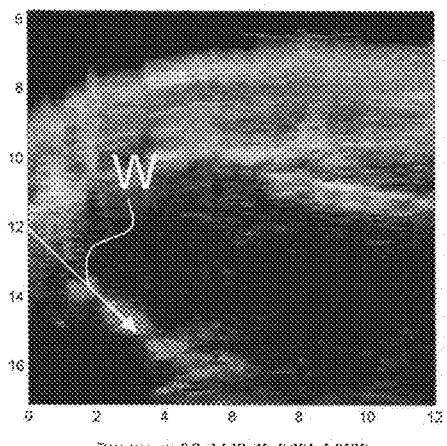
Figure 26I:
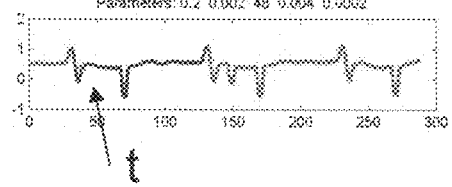
Figure 26E:
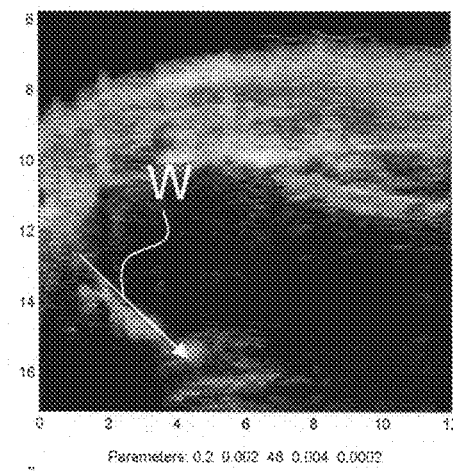
Figure 26J:
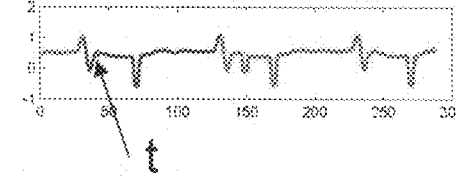
Figure 27A:
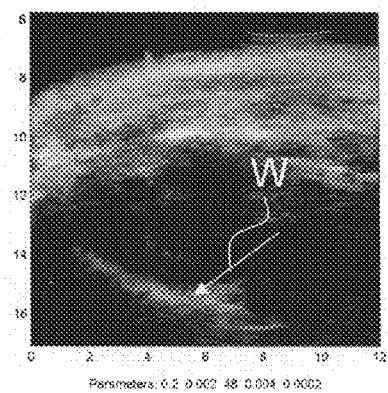
FIGS. 27(a)-(e) illustrate a sequence of axial displacement maps overlaid to the grayscale image (0.07 ms between successive frames) indicating an electromechanical wave propagating in the posterior wall of the mouse from the base towards theapex during pacing in the right ventricle close to the base in accordance with the present invention.
Figure 27B:
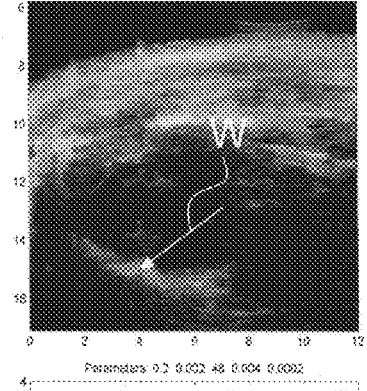
Figure 27F:
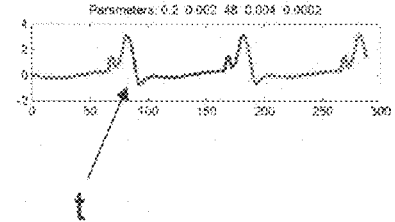
FIGS. 27(f)-(j) illustrate the ECG signal plotted below each respective image of FIGS. 27(a)-(e) indicating the time t of the acquisition during the cardiac cycle in accordance with the present invention.
Figure 27G:
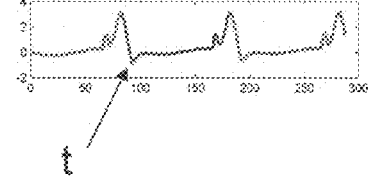
Figure 27C:
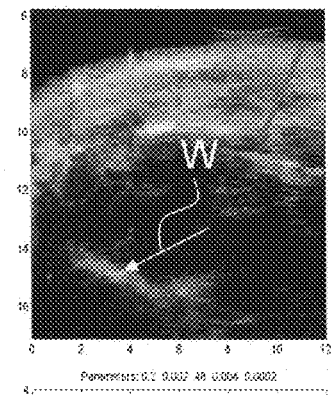
Figure 27H:
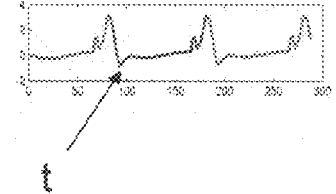
Figure 27D:
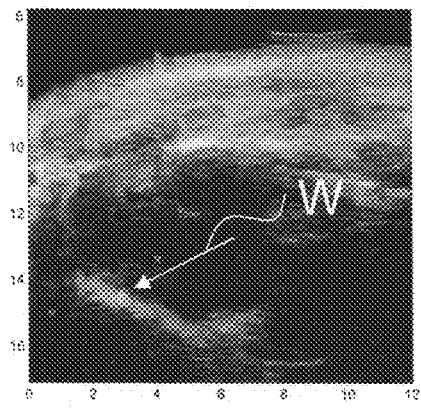
Figure 27I:
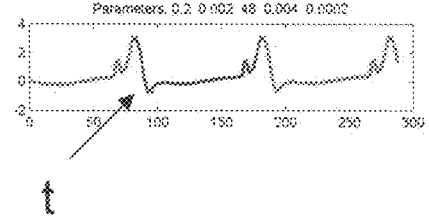
Figure 27E:
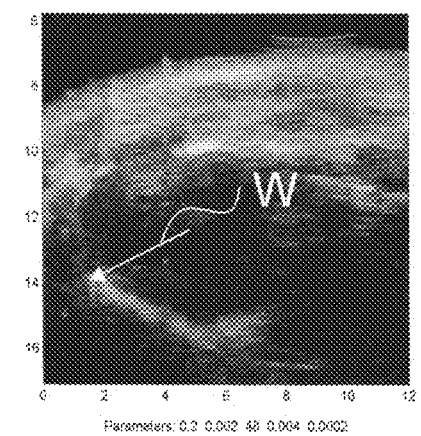
Figure 27J:
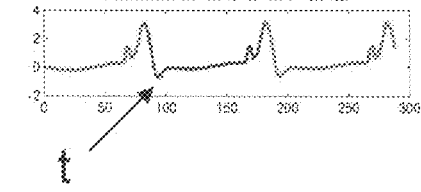
Figure 28A:
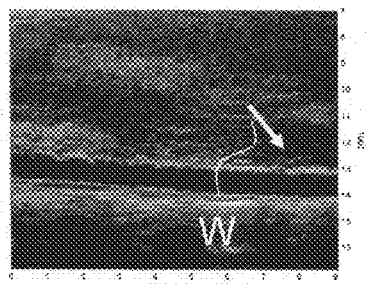
FIGS. 28(a)-(f) illustrate a sequence of axial displacement maps overlaid to the grayscale B-mode image of the aorta taken every 0.7 ms. Sequence of images showing the propagation of the pulse wave in the aorta. The arrows indicate the progression of the wave front in the aorta.
Figure 28B:
Figure 28G:
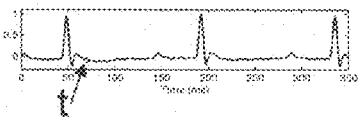
FIGS. 28(g)-(l) illustrate the ECG signal plotted below each respective image of FIGS. 26(a)-(f) indicating the time t of the acquisition during the cardiac cycle in accordance with the present invention.
Figure 28H:
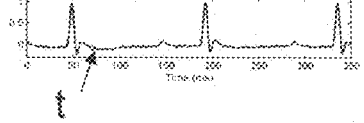
Figure 28C:
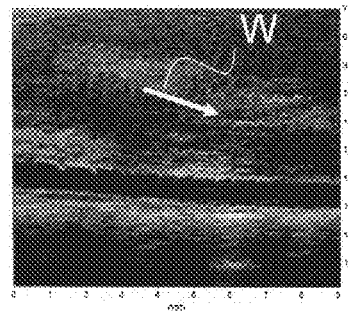
Figure 28D:
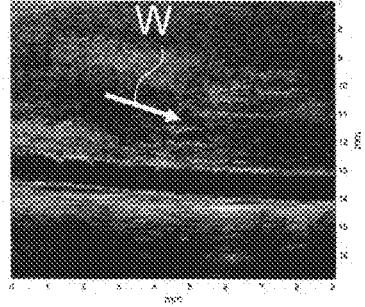
Figure 28I:
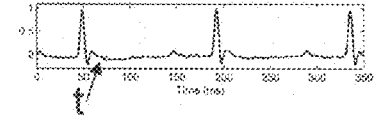
Figure 28J:
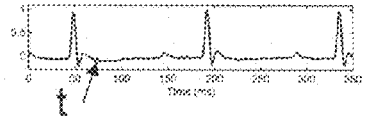
Figure 28E:
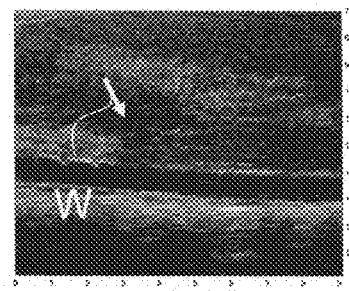
Figure 28F:
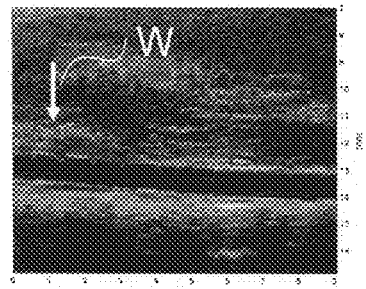
Figure 28K:
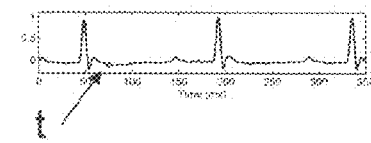
Figure 28L:
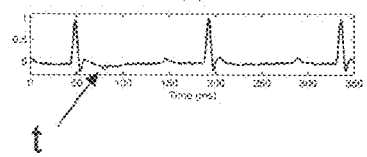

However, the FIG. 24 shows a wave propagating in the posterior wall (see the white arrows W). The displacements were initiated at the apex (left side of the images) and then propagated towards the base (right side). The phase velocity was determined using the method previously described at the frequency of 80 Hz. The distance of propagation was plotted in FIG. 25 as a function of the phase of the wave divided by the angular frequency. The phase velocity of the wave was obtained using a linear regression fit and was estimated to be 0.44 m/s.

Imaging Under Different Electrical Pacing Conditions

In order to determine that the origin and direction of the wave W were electrically induced and driven, mice were also scanned during right-atrial pacing (at 90 ms corresponding to a heart cycle at sinus rhythm of 100 ms period; FIGS. 26(a)-(e)) and right-ventricular pacing (also at 90 ms; FIGS. 27(a)-(e)). Pacing was achieved using catheterization through the right side of the heart, in which the catheter carried nine electrodes that could be separately activated for varying the pacing location. In some of the scans, the catheter C was within the imaging field-of-view and allowed for imaging of the pacing wave during ventricular pacing (FIGS. 26(c) and 27(c)).

The most pronounced wave propagating during atrial pacing was the contraction wave, or wave originating at the isovolumic contraction phase, that propagated along the longitudinal direction of the myocardium initiating radial thickening (or, positive (red) displacement) in its path. At atrial pacing (FIG. 26(a)-(e)), the contraction wave was very similar to the one during sinus rhythm (FIGS. 24(a)-(f)), starting at the apex right at the QRS peak and then propagating along the posterior wall (generally from right to left in the figure.) Right-ventricular pacing (FIGS. 27(a)-(e)) induced a reverse direction on the contraction wave that now started from the tip of the catheter (close to the base) with two waves propagating from base to apex, one along the septum and one along the posterior wall (generally from left to right in the figure) (FIG. 27(a)-(e)). Since pacing occurred using the same mouse, same sonographic view and without affecting the function of the valves or the blood flow, the reverse direction of the propagation of the wave is concluded to be induced by the change in the origin of the electrical stimulus; thereby, confirming that the wave measured is electrically induced.

In Vivo Vascular Imaging

A longitudinal view of the abdominal aorta of a mouse was imaged using the high frame rate technique. Axial displacements were calculated, and the movie of the motion was processed at 8000 fps for a complete cardiac cycle. During the cardiac cycle, the displacements of the artery wall were found to be very small except after the beginning of systole. Strong displacements of the wall started 10.3 ms after the R-wave peak of the ECG. FIGS. 28(a)-(f) show a sequence of the axial displacements in color overlaid onto the grayscale B-mode image. A transverse wave W started propagating on the right side of the images (heart side) and then propagated towards the left side in less than 3 ms. This transverse wave was generated from the sudden pressure change of the blood bolus traveling through the vessel, known as the arterial pulsive wave (Nichols and O'Rourke 1998).

Figure 29:
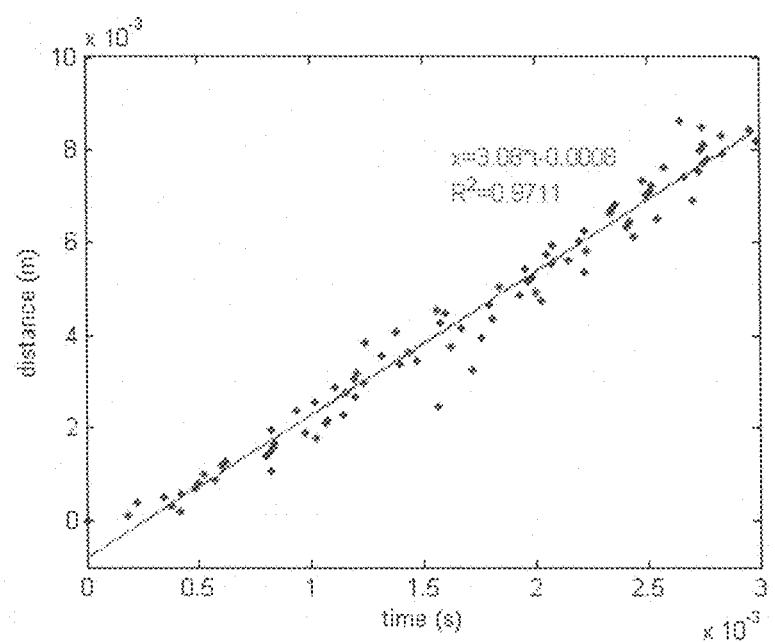
FIG. 29 illustrates the distance of propagation as a function of the phase of pulse wave at the frequency of 80 Hz. The slope of the curve gives the pulse wave velocity in accordance with the present invention.

The phase velocity of the pulse wave was computed at the frequency of 200 Hz. The distance of propagation was plotted in FIG. 29 as a function of the phase of the wave divided by the angular frequency, the phase velocity was obtained using a linear regression fit and was found to be 3.08 m/s. The radius of the vessel R=0.47 mm and the wall thickness h=0.12 mm were approximately estimated from the B-mode images, and the blood density was assumed to be 1060 kg/m$^3$ (Cutnell and Kenneth 1998). Using these parameters, the Young's modulus of the aorta wall E=78.8 kPa was derived from the Moens- Korteweg equation (Eq. 5), which is what has been typically reported for thoracic aorta moduli in biomechanics literature (Fung 1993).

Various references are cited herein, the contents of which are hereby incorporated by reference in their entireties.

Avolio, A. P., S. G. Chen, R. P. Wang, C. L. Zhang, M. F. Li and M. F. O'Rourke. Effects of aging on changing arterial compliance and left ventricular load in a northern Chinese urban community. Circulation (1983) 68(1): 50-8.

Berne, R. M. and M. N. Levy (1992). Cardiovascular Physiology. St. Louis, Mo.

Bonnefous, O. and P. Pesque. Time domain formulation of pulse-Doppler ultrasound and blood velocity estimation by cross correlation. Ultrason Imaging (1986) 8(2): 73-85.

Bercoff, J., Tanter, M., and Fink, M. (2004). Supersonic shear imaging: A new technique for soft tissue elasticity mapping. *IEEE Transactions on Ultrasonics Ferroelectrics and Frequency Control* 51, 396-409.

Brooks, D. H., and MacLeod, R. S. (1997). Electrical imaging of the heart. *Ieee Signal Processing Magazine* 14, 24-42.

Chubachi, N., Kanai, H., and Koiwa, Y. (1997). Ultrasonic diagnostic equipment. Japan.

Cutnell, J. and W. Kenneth (1998). Physics, Fourth Edition. New York.

Declerck, J., T. S. Denney, C. Ozturk, W. O'Dell and E. R. McVeigh. Left ventricular motion reconstruction from planar tagged MR images: a comparison. Phys Med Biol (2000) 45(6): 1611-1632.

Edwards, C. H., Rankin, J. S., Mchale, P. A., Ling, D., and Anderson, R. W. (1981). Effects of Ischemia on Left-Ventricular Regional Function in the Conscious Dog. *American Journal of Physiology* 240, H413-H420.

Fung, Y. C. (1993). Biomechanics—Mechanical Properties of Living Tissues. New York.

Greenwald, S. E. Pulse pressure and arterial elasticity. Qjm-an International Journal of Medicine (2002) 95(2): 107-112.

Gupta, K. B., Ratcliffe, M. B., Fallert, M. A., Edmunds, L. H., and Bogen, D. K. (1994). Changes in Passive Mechanical Stiffness of Myocardial Tissue with Aneurysm Formation. *Circulation* 89, 2315-2326.

Heimdal, A., A. Stoylen, H. Torp and T. Skjaerpe. Real-time strain rate imaging of the left ventricle by ultrasound. J Am Soc Echocardiog (1998) 11(11): 1013-1019.

Henderso, A., Parmley, W. W., and Sonnenbl, E. (1971). Series Elasticity of Heart Muscle During Hypoxia. *Cardiovascular Research* 5, 10-&.

Kanai, H. Propagation of spontaneously actuated pulsive vibration in human heart wall and in vivo viscoelasticity estimation. Ieee T Ultrason Ferr (2005) 52(11): 1931-1942.

Kanai, H. and Y. Koiwa. Myocardial rapid velocity distribution. Ultrasound Med Biol (2001) 27(4): 481-498.

Kanai, H., H. Satoh, K. Hirose and N. Chubachi. A New Method for Measuring Small Local Vibrations in the Heart Using Ultrasound. Ieee T Bio-Med Eng (1993) 40(12): 1233-1242.

Kanai, H., A. Umezawa and Y. Koiwa (2000). Transcutaneous measurement of frequency dispersion in the regional pulse wave velocity. IEEE Ultrasonics symposium.

Konofagou, E. E., J. D'Hooge and J. Ophir. Myocardial elastography—A feasibility study in vivo. Ultrasound Med Biol (2002) 28(4): 475-482.

Konofagou E. E. and Ophir, J., (1998) A New Elastographic Method for Estimation and Imaging of Lateral Strains, Corrected Axial Strains and Poison's Ratios in Tissues, *Ultrasound in Medicine and Biology* 24(8), 1183-1199.

Konofagou E. E., Kallel F. and Ophir J., (1998) Three-dimensional Motion estimation in Elastography, IEEE Proceedings of the Symposium of Ultrasonics, Ferroelectrics and Frequency Control in Sendai, Japan, 1745-1748.

Korteweg, D. Uber die Fortpflanzungsgeschwindigkeit des Schalles in elastichen Rohren. Ann. Phys. Chem. (1879) 5: 525-37.

Landau, L. D. and E. M. Liftshitz (1965). Theory of elasticity. Moscow.

McLaughlin, J., M. McNeill, B. Braun and P. D. McCormack. Piezoelectric sensor determination of arterial pulse wave velocity. Physiol Meas (2003) 24(3): 693-702.

Moens, A. (1879). Die Pulsekurve. Leiden.

Nichols, W. and M. F. O'Rourke (1998). Vascular impedance.In McDonald's: blood flow in arteries: theoretical, experimental and clinical principles. E. Arnold. London.

Rogers, W. J., Y. L. Hu, D. Coast, D. A. Vido, C. M. Kramer, R. E. Pyeritz and N. Reichek. Age-associated changes in regional aortic pulse wave velocity. J Am Coll Cardiol (2001) 38(4): 1123-9.

Roth, B. J. (2000). Influence of a perfusing bath on the foot of the cardiac action potential. *Circulation Research* 86, E19-E22.

Sandrin, L., S. Catheline, M. Tanter, X. Hennequin and M. Fink. Time-resolved pulsed elastography with ultrafast ultrasonic imaging. Ultrason Imaging (1999) 21(4): 259-72.

Sarvazyan, A. P., O. V. Rudenko, S. D. Swanson, J. B. Fowlkes and S. Y. Emelianov. Shear wave elasticity imaging: A new ultrasonic technology of medical diagnostics. Ultrasound Med Biol (1998) 24(9): 1419-1435.

Sinkus, R., J. Lorenzen, D. Schrader, M. Lorenzen, M. Dargatz and D. Holz. High-resolution tensor MR elastography for breast tumour detection. Phys Med Biol (2000) 45(6): 1649-1664.

Spach, M. S., Heidlage, J. F., Dolber, P. C., and Barr, R. C. (1998). Extracellular discontinuities in cardiac muscle—Evidence for capillary effects on the action potential foot. *Circulation Research* 83, 1144-1164.

Sutherland, G. R. Color Doppler Myocardial Imaging—Potential Applications in Acquired and Congenital Heart-Disease. Acta Paediatr (1995) 84: 40-48.

Tanter, M., J. Bercoff, L. Sandrin and M. Fink. Ultrafast compound imaging for 2-D motion vector estimation: application to transient elastography. IEEE Trans Ultrason Ferroelectr Freq Control (2002) 49(10): 1363-74.

Walker, W. F. and G. E. Trahey. A Fundamental Limit on Delay Estimation Using Partially Correlated Speckle Signals. Ieee T Ultrason Ferr (1995) 42(2): 301-308.

Wang, Y. X., M. Halks-Miller, R. Vergona, M. E. Sullivan, R. Fitch, C. Mallari, B. Martin-McNulty, V. da Cunha, A. Freay, G. M. Rubanyi and K. Kauser. Increased aortic stiffness assessed by pulse wave velocity in apolipoprotein E-deficient mice. Am J Physiol Heart Circ Physiol (2000) 278(2): H428-34.

Young, T. On the functions of the heart and arteries. Philos Trans (1809) 99: 1-31.

Zerhouni, E. A., D. M. Parish, W. J. Rogers, A. Yang and E. P. Shapiro. Human heart: tagging with MR imaging—a method for noninvasive assessment of myocardial motion. Radiology (1988) 169(1): 59-63.

It will be understood that the foregoing is only illustrative of the principles of the invention, and that various modifications can be made by those skilled in the art without departing from the scope and spirit of the invention.

APPENDIX

A portion of the disclosure of this patent document contains material which is subject to copyright protection. The copyright owner has no objection to the facsimile reproduction by anyone of any portion of the patent document, as it appears in any patent granted from the present application or in the Patent and Trademark Office file or records available to the public, but otherwise reserves all copyright rights whatsoever.

A computer program listing is submitted in duplicate on two identical CD-Roms. Each CD-Rom contains several routines which are listed in the Appendix. The CD was created on May 12, 2006. The files on the CD are incorporated by reference in their entirety herein.

MULTIFRAME
FuncCalculDispl
CORRELATION2D.CPP
OVERLAY
TRACK POSITION WAVE
IMAGERF1
FILTRE3D

What is claimed is:

1. A method for directly detecting an electromechanical wave propagation within a body structure of a subject, comprising:
scanning, using ultrasound, said body structure during a predefined interval to acquire image data comprising a series of image frames directly representing the electromechanical wave, the series dividing a duration of the electromechanical wave, the scanning including a path along which the electromechanical wave propagates;
performing a correlation calculation on the image frames to generate one or more correlation matrices representing relative displacements between successive image frames;
detecting parameters of the electromechanical wave propagation within said body structure by analyzing the relative displacements in said correlation matrices; and
generating a video graphically representing the body structure and the progression of the electromechanical wave over said path,
wherein:
the body structure includes at least a portion of a myocardium, artery, or aorta;
the electromechanical wave:
is a transient deformation arising directly from an electrical wave propagation in the body structure;
propagates along a path of, during the predefined interval of, and in parallel itinerary with, the electrical wave propagation;
the scanning is performed without inducement of motion other than the electromechanical wave representable as the displacements in said correlation matrices;
the parameters include a time sequence of locations of a front of the electromechanical wave represented in the series of image frames; and
the detecting includes:
determining magnitudes of said relative displacements;
selecting ones of the relative displacements occurring in said predetermined interval that possess magnitudes representative of the electromechanical wave; and
estimating the time sequence of locations from the selected ones of the displacements.

2. The method according to claim 1, wherein the at least a portion is a myocardium of the subject.

3. The method according to claim 1, wherein the at least a portion is an artery of the subject.

4. The method according to claim 1, wherein the at least a portion is an aorta of the subject.

5. The method according to claim 1, wherein the scanning to acquire image data comprises acquiring multiple sets of ultrasound image data which are separated by at least one cardiac cycle and merged into a single sequence by reference to a common reference point of the cardiac cycle.

6. The method according to claim 1, wherein scanning to acquire image data comprises acquiring image data at a frame rate of between 50 and 56 frames per second.

7. The method according to claim 1, wherein the performing of the correlation calculation further comprises applying a noise threshold.

8. The method according to claim 1, wherein the detecting parameters of the electromechanical wave propagation within said body structure comprises detecting contractile movement of said body structure.

9. The method according to claim 1, wherein the performing of the correlation calculation comprises applying a cross-correlation, auto-correlation, or coherence calculation.

10. The method according to claim 1, wherein detecting parameters of the electromechanical wave propagation within said body structure comprises detecting a location where adjacent portions of the body structure move in opposing directions on said correlation matrices, whereby the front of the electromechanical wave is detected, and wherein the generating of the video includes highlighting the detected front of the electromechanical wave.

11. The method according to claim 1, wherein the generating of the video includes generating a video comprising a series of images representing the relative displacements.

12. A method for directly detecting an electromechanical wave propagation within a body structure of a subject comprising:
using an ultrasound imaging device, positioned and oriented to scan at least a portion of a path;
scanning said body structure during a predefined interval to acquire image data comprising a series of image frames directly representing the electromechanical wave, wherein said electromechanical wave is not induced by said acquiring;
performing a correlation calculation on the image frames to generate one or more correlation matrices representing relative displacements between successive image frames;
detecting parameters of the electromechanical wave propagation within said body structure by analyzing the relative displacements in said correlation matrices, the parameters including at least one of velocity as a function of at least one of location and time, relative displacement as a function of time, and position of a forward edge of the electromechanical wave as a function of time; and
displaying a graphical representation of the body structure and said parameters,
wherein the body structure includes at least a portion of a myocardium, artery, or aorta, and the electromechanical wave is a transient deformation occurring over a path of, and during the predefined interval of, an electrical wave propagation.

13. The method according to claim 12, wherein acquiring image data comprises acquiring image data at a frame rate of between 50 and 56 frames per second.

14. The method according to claim 12, wherein the performing of the correlation calculation further comprises applying a noise threshold.

15. The method according to claim 12, wherein detecting parameters of the electromechanical wave propagation within said body structure comprises detecting contractile movement of said body structure.

16. The method according to claim 12, wherein performing the correlation calculation comprises applying a cross-correlation, auto-correlation, or coherence calculation.

17. The method according to claim 12, wherein detecting parameters of the electromechanical wave propagation within said body structure comprises performing a zero-crossing algorithm on said correlation matrices.

18. The method according to claim 12, further comprising generating a video comprising a series of images representing the relative displacements.

19. The method according to claim 1, further comprising generating a video comprising a series of images representing strains.

20. The method according to claim 1, further comprising generating a video comprising a series of images representing strain rates.

21. The method according to claim 1, wherein said scanning is performed to acquire image data at a rate commensurate with a speed of propagation of the electromechanical wave.

22. The method of claim 1, further comprising, responsively to the video, determining in vivo an electrical propagation in a myocardium and positioning a pacemaker responsively to a result of the determining.

23. The method of claim 12, further comprising, responsively to the displaying the parameters, determining in vivo an electrical propagation in a myocardium and positioning a pacemaker responsively to a result of the determining.

24. The method of claim 1, further comprising, responsively to a result of the detecting, at least one of diagnosing and surgically treating: a conduction disturbance in a heart of a patient, arrhythmias and dysrhythmias, or tissue abnormalities associated with cardiomyopathies or trauma.

25. The method of claim 12, further comprising, responsively to a result of the detecting, at least one of diagnosing and surgically treating: a conduction disturbance in a heart of a patient, arrhythmias and dysrhythmias, or tissue abnormalities associated with cardiomyopathies or trauma.

26. A sequence of programmed instructions stored in a non-transitory computer readable medium for directly detecting an electromechanical wave propagation within a body structure of a subject, the instructions being executed by a computer processing system, comprising:

scanning, using ultrasound, said body structure during a predefined interval to acquire image data comprising a series of image frames directly representing the electromechanical wave, the series dividing a duration of the electromechanical wave, the scanning including a path along which the electromechanical wave propagates;

performing a correlation calculation on the image frames to generate one or more correlation matrices representing relative displacements between successive image frames;

detecting parameters of the electromechanical wave propagation within said body structure by analyzing the relative displacements in said correlation matrices;

and generating a video graphically representing the body structure and the progression of the electromechanical wave over said path, wherein:
the body structure includes at least a portion of a myocardium, artery, or aorta;
the electromechanical wave:
is a transient deformation arising directly from an electrical wave propagation in the body structure;
propagates along a path of, during the predefined interval of, and in parallel itinerary with, the electrical wave propagation;
detecting parameters of the electromechanical wave propagation within said body structure by analyzing relative displacements in said correlation matrices;
the scanning is performed without inducement of motion other than the electromechanical wave representable as the displacements in said correlation matrices;
the parameters include a time sequence of locations of a front of the electromechanical wave represented in the series of image frames; and
the detecting includes:
determining magnitudes of said relative displacements;
selecting ones of the relative displacements occurring in said predetermined interval that possess magnitudes representative of the electromechanical wave; and
estimating the time sequence of locations from the selected ones of the displacements.

27. The sequence of programmed instructions according to claim 26, wherein the scanning to acquire image data comprises acquiring multiple sets of ultrasound image data which are separated by at least one cardiac cycle and merged into a single sequence by reference to a common reference point of the cardiac cycle.

28. The sequence of programmed instructions according to claim 26, wherein the detecting parameters of the electromechanical wave propagation within said body structure comprises detecting contractile movement of said body structure.

29. The sequence of programmed instructions according to claim 26, wherein detecting parameters of the electromechanical wave propagation within said body structure comprises detecting a location where adjacent portions of the body structure move in opposing directions on said correlation matrices, whereby the front of the electromechanical wave is detected, and wherein the generating of the video includes highlighting the detected front of the electromechanical wave.

30. The sequence of programmed instructions according to claim 26, wherein the generating of the video includes generating a video comprising a series of images representing the relative displacements.

* * * * *